(12) United States Patent
Giuliani et al.

(10) Patent No.: US 7,700,119 B2
(45) Date of Patent: Apr. 20, 2010

(54) 85KDA NEISSERIAL ANTIGEN

(75) Inventors: Marzia Monica Giuliani, Siena (IT); Mariagrazia Pizza, Siena (IT); Rino Rappuoli, Castelnuovo Berardenga (IT); Johan Holst, Oslo (NO)

(73) Assignee: Novartis Vaccines and Diagnostics SRL, Siena (IT)

( * ) Notice: Subject to any disclaimer, the term of this patent is extended or adjusted under 35 U.S.C. 154(b) by 503 days.

(21) Appl. No.: 11/264,676

(22) Filed: Nov. 1, 2005

(65) Prior Publication Data

US 2006/0233827 A1 Oct. 19, 2006

Related U.S. Application Data

(62) Division of application No. 10/148,534, filed as application No. PCT/IB00/01851 on Nov. 28, 2000.

(30) Foreign Application Priority Data

Nov. 29, 1999 (GB) ................... 9928197.4
Mar. 9, 2000 (GB) ................... 0005698.6

(51) Int. Cl.
*A61K 39/095* (2006.01)
*C07H 21/04* (2006.01)
*C12P 21/04* (2006.01)
*C07K 14/00* (2006.01)

(52) U.S. Cl. ............... 424/250.1; 424/184.1; 435/69.1; 435/69.7; 435/252.3; 530/350; 536/23.5; 536/23.7

(58) Field of Classification Search ................. None
See application file for complete search history.

(56) References Cited

U.S. PATENT DOCUMENTS 6,610,306 B2 * 8/2003 Judd et al. ............... 424/250.1

FOREIGN PATENT DOCUMENTS

| WO | WO 90/06696 A2 | 6/1990 |
|---|---|---|
| WO | WO 95/03413 A1 | 2/1995 |
| WO | WO 96/29412 A1 | 9/1996 |
| WO | WO 97/28273 A1 | 8/1997 |
| WO | WO 99/24578 A2 | 5/1999 |
| WO | WO 99/31132 A1 | 6/1999 |
| WO | WO 99/36544 A2 | 7/1999 |
| WO | WO 99/57280 A2 | 11/1999 |
| WO | WO-0022430 | 4/2000 |
| WO | WO-0023595 | 4/2000 |
| WO | WO-0050075 | 8/2000 |

OTHER PUBLICATIONS

Greenspan et al (Nature Biotechnology, 1999, 7:936-937).*
Houghten et al. (Vaccines, 1986, Edited by Fred Brown: Cold Spring Harbor Laboratory).*
Holmes, Exp. Opin.Invest. Drugs, 2001, 10(3):511-519).*
Ala'Aldeen et al., "The meningococcal transferrin-binding proteins 1 and 2 are both surface exposed and generate bactericidal antibodies capable of killing homologous and heterologous strains," *Vaccine* 14(1):49-53, 1996.
Fredriksen et al., "Production, characterization and control of MenB-vaccine <<Folkehelsa>>: an outer membrane vesicle vaccine against group B meningococcal disease," *NIPH Ann* 14(2):67-80, 1991.
HØiby et al., "The norwegian meningococcal serogroup B outer membrane vesicle vaccine protection trials: case tracing, meningococcal antigen detection and serological diagnosis,"*NIPH Annals* 14(2):107-123, 1991.
Manning et al., "OMP85 Proteins of Neisseria gonorrhoeae and Neisseria meningitidis are similar to Haemophilus influenzae D-15-AG and Pasteurella multocida OMA87," *Microbial Pathogenesis* 25(1):11-21, 1998.
Poolman, "Development of a meningococcal vaccine," *Infect. Agents Dis.* 4:13-28, 1995.
Romero et al., "Current Status of meningococcal group B vaccine candidates: capsular or noncapsular?" *Clin Microbial. Rev.* 7(4):559-575, 1994.
EMPRO Database Accession No. AF021245. Manning et al. (Oct. 7, 1997). "Neisseria meningitis outer membrane protein (omp85) gene, complete cds." 3 pages.

* cited by examiner

*Primary Examiner*—Robert B Mondesi
*Assistant Examiner*—Padma V Baskar
(74) *Attorney, Agent, or Firm*—Amy Hessler; Helen Lee; Robert Corman

(57) ABSTRACT

An 85 kDa antigen from *Neisseria meningitidis* and *Neisseria gonorrhoeae* has been cloned, sequenced and expressed. The antigen is common to diverse strains, serogroups and serotypes of *N. meningitidis*, and also to *N. gonorrhoeae*, *N. polysaccharia* and *N. lactamica*. The protein sequences of *N. meningitidis* (serogroups A and B) and *N. gonorrhoeae* are highly homologous.

3 Claims, 9 Drawing Sheets

FIGURE 1

Leader sequence          orf21.pep

```
  1  MKLKQIASAL MMLGISPLAL ADFTIQDIRV EGLQRTEPST VFNYLPVKVG
 51  DTYNDTHGSA IIKSLYATGF FDDVRVETAD GQLLLTVIER PTIGSLNITG
101  AKMLQNDAIK KNLESFGLAQ SQYFNQATLN QAVAGLKEEY LGRGKLNIQI
151  TPKVTKLARN RVDIDITIDE GKSAKITDIE FEGNQVYSDR KLMRQMSLTE
201  GGIWTWLTRS NQFNEQKFAQ DMEKVTDFYQ NNGYFDFRIL DTDIQTNEDK
251  TKQTIKITVH EGGRFRWGKV SIEGDTNEVP KAELEKLLTM KPGKWYERQQ
301  MTAVLGEIQN RMGSAGYAYS EISVQPLPNA ETKTVDFVLH IEPGRKIYVN
351  EIHITGNNKT RDEVVRRELR QMESAPYDTS KLQRSKERVE LLGYFDNVQF
401  DAVPLAGTPD KVDLNMSLTE RSTGSLDLSA GWVQDTGLVM SAGVSQDNLF
451  GTGKSAALRA SRSKTTLNGS LSFTDPYFTA DGVSLGYDVY GKAFDPRKAS
501  TSIKQYKTTT AGAGIRMSVP VTEYDRVNFG LVAEHLTVNT YNKAPKHYAD
551  FIKKYGKTDG TDGSFKGWLY KGTVGWGRNK TDSALWPTRG YLTGVNAEIA
601  LPGSKLQYYS ATHNQTWFFP LSKTFTLMLG GEVGIAGGYG RTKEIPFFEN
651  FYGGGLGSVR GYESGTLGPK VYDEYGEKIS YGGNKKANVS AELLFPMPGA
701  KDARTVRLSL FADAGSVWDG KTYDDNSSSA TGGRVQNIYG AGNTHKSTFT
751  NELRYSAGGA VTWLSPLGPM KFSYAYPLKK KPEDEIQRFQ FQLGTTF*
```

ATP/GTP-binding site motif A (P-loop)

Isoelectric Point – 9.50

Molecular Weight – 88.5 kDa

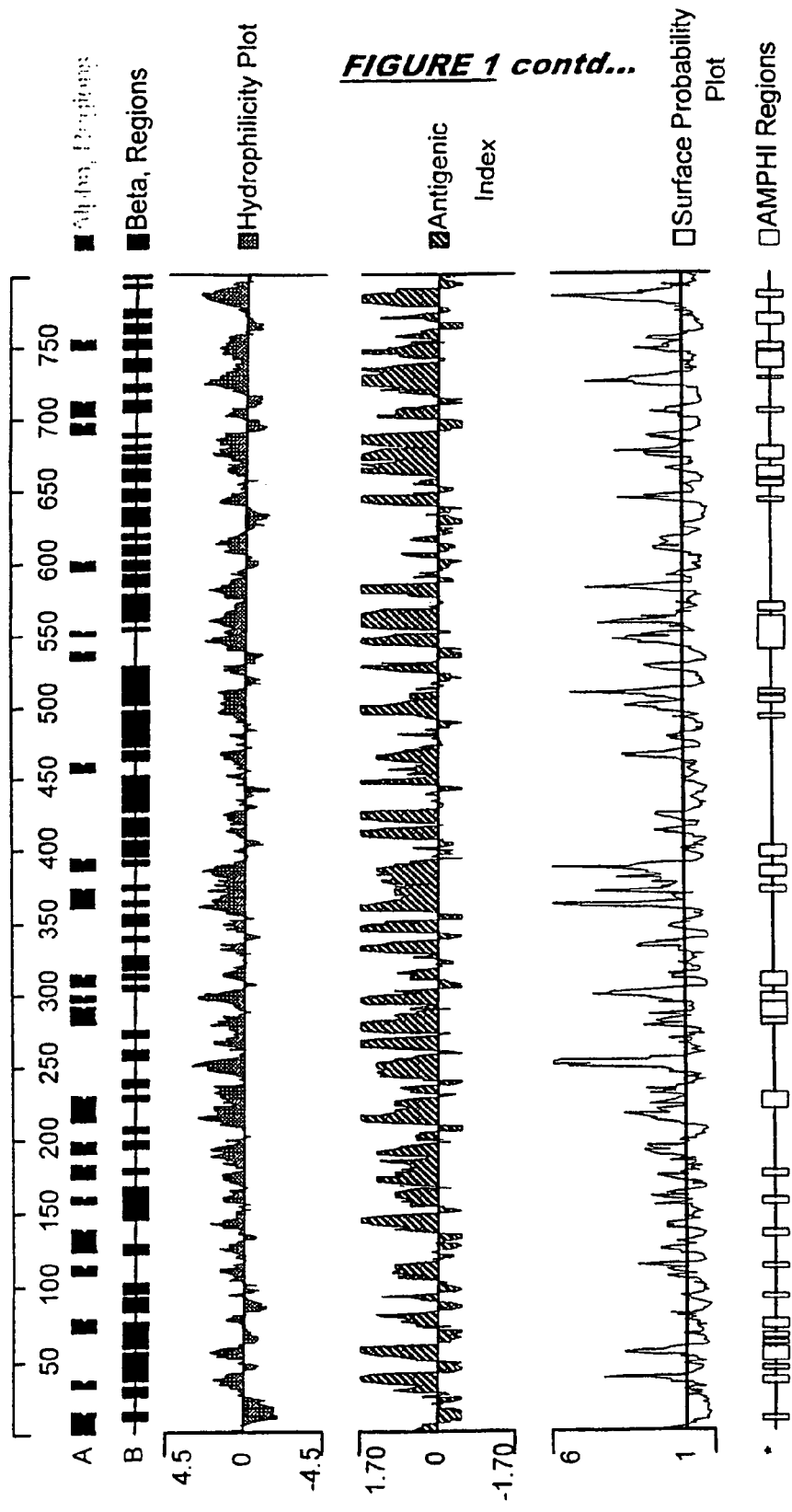

FIGURE 1 contd...
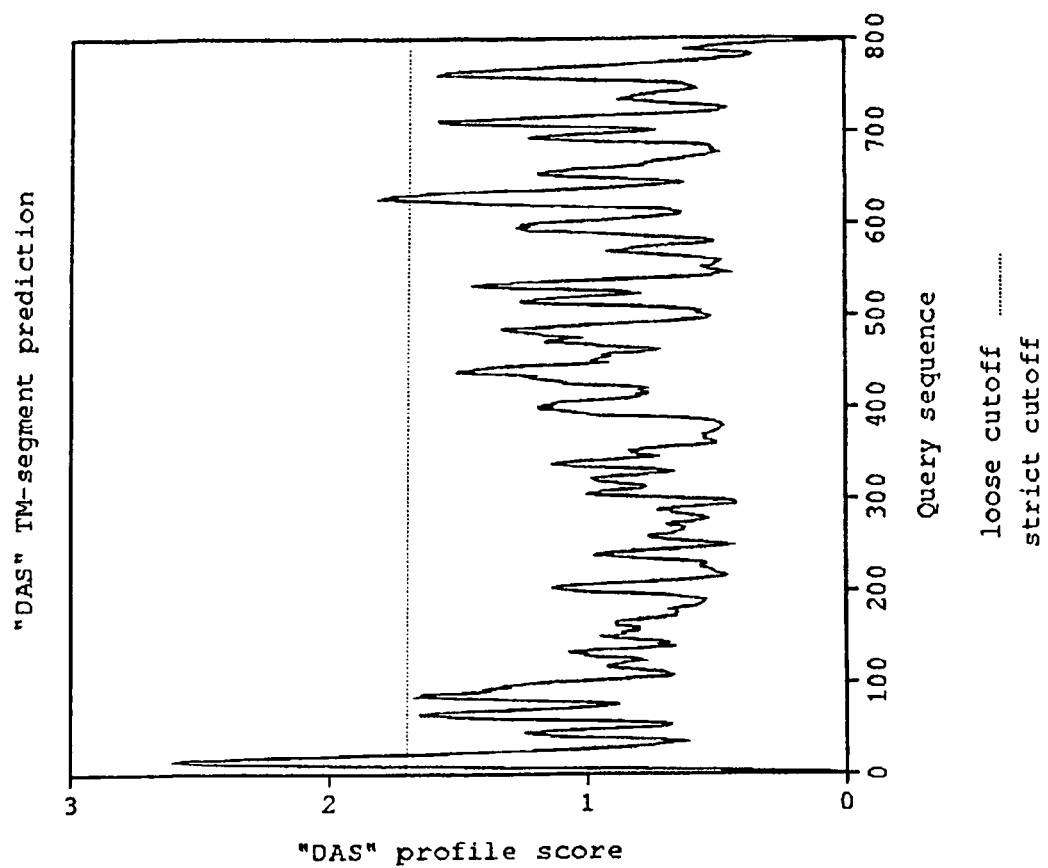

Levels of identity:

ORF21_B / ORF21_A : 98.3% over 2394bp
ORF21_B / OMP85 : 98.2% over 2394bp
ORF21_B / ORF21_NG : 95% over 2187bp

85KDA NEISSERIAL ANTIGEN

This application is a divisional application of U.S. application Ser. No. 10/148,534, filed Oct. 9, 2002 abandoned subsequent to the filing of the present application, which is the National Stage of International Application No. PCT/IB00/01851, filed Nov. 28, 2000, which claims the benefit under 35 U.S.C. 119(a) of foreign applications GB 9928197.4, filed Nov. 29, 1999 and GB 0005698.6, filed Mar. 9, 2000, all of which applications are hereby incorporated herein by reference in their entireties.

All documents cited herein are hereby incorporated by reference in their entirety.

TECHNICAL FIELD

This invention relates to an antigen from the related bacteria *Neisseria meningitidis* and *Neisseria gonorrhoeae*.

BACKGROUND ART

*Neisseria meningitidis* is a non-motile, Gram-negative diplococcus human pathogen. It colonises the pharynx, causing meningitis and, occasionally, septicaemia in the absence of meningitis. It is closely related to *N. gonorrhoeae*, although one feature that clearly differentiates meningococcus from gonococcus is the presence of a polysaccharide capsule that is present in all pathogenic meningococci.

*N. meningitidis* causes both endemic and epidemic disease. In the United States the attack rate is 0.6-1 per 100,000 persons per year, and it can be much greater during outbreaks [Lieberman et al. (1996) *JAMA* 275(19):1499-1503; Schuchat et al (1997) *N Engl J Med* 337(14):970-976]. In developing countries, endemic disease rates are much higher and during epidemics incidence rates can reach 500 cases per 100,000 persons per year. Mortality is extremely high, at 10-20% in the United States, and much higher in developing countries. Following the introduction of the conjugate vaccine against *Haemophilus influenzae*, *N. meningitidis* is the major cause of bacterial meningitis at all ages in the United States [Schuchat et al (1997) supra].

Based on the organism's capsular polysaccharide, 12 serogroups of *N. meningitidis* have been identified. The meningococcal vaccine currently in use is a tetravalent polysaccharide vaccine composed of serogroups A, C, Y and W135. Following the success of the vaccination against *H. influenzae*, however, conjugate vaccines against serogroups A and C have been developed Meningococcus B remains a problem, however. This serotype currently is responsible for approximately 50% of total meningitis in the United States, Europe, and South America. The polysaccharide approach cannot be used because the menB capsular polysaccharide is a polymer of α(2-8)-linked N-acetyl neuraminic acid that is also present in mammalian tissue. This results in tolerance to the antigen; indeed, if a response were elicited, it would be anti-self, and therefore undesirable. In order to avoid induction of autoimmunity and to induce a protective immune response, the capsular polysaccharide has, for instance, been chemically modified substituting the N-acetyl groups with N-propionyl groups, leaving the specific antigenicity unaltered [Romero & Outschoorn (1994) *Clin Microbiol Rev* 7(4):559-575].

Alternative approaches to menB vaccines have used complex mixtures of outer membrane proteins (OMPs), containing either the OMPs alone, or OMPs enriched in porins, or deleted of the class 4 OMPs that are believed to induce antibodies that block bactericidal activity. These vaccines are poorly characterised and are only effective against homologous strains. To overcome antigenic variability, multivalent vaccines containing up to nine different porins have been constructed [e.g. Poolman J T (1992) *Infect. Agents Dis.* 4:13-28]. Additional proteins to be used in outer membrane vaccines have been the opa and opc proteins, but none of these approaches have been able to overcome the antigenic variability [e.g. Ala'Aldeen & Borriello (1996) *Vaccine* 14(1):49-53]. The Norwegian National Institute of Public Health vaccine, however, is safe, elicits strain-specific immunity in children and adults, and is efficacious in preventing disease in adolescents [Fredriksen et al. (1991) *NIPH Ann* 14(2):67-80 & 107-123].

These vaccines are, however, poorly characterised, and the molecular basis for their efficacy and protection has not been dissected. It is an object of the present invention to define antigenic components of vaccines, to characterise them in order to allow better defined vaccines to be produced (e.g. acellular sub-unit vaccines), and to broaden the *Neisseria* strains against which immunity is elicited.

BRIEF DESCRIPTION OF THE DRAWINGS

FIG. 1 shows the sequence of ORF21, together with computer analysis data including: the isoelectric point, the molecular weight, alpha helical regions, beta sheet regions, a hydrophilicity plot, an antigenic index, a surface probability plot, AMPHI regions, and "DA" transmembrane segment prediction.

Figure 2:
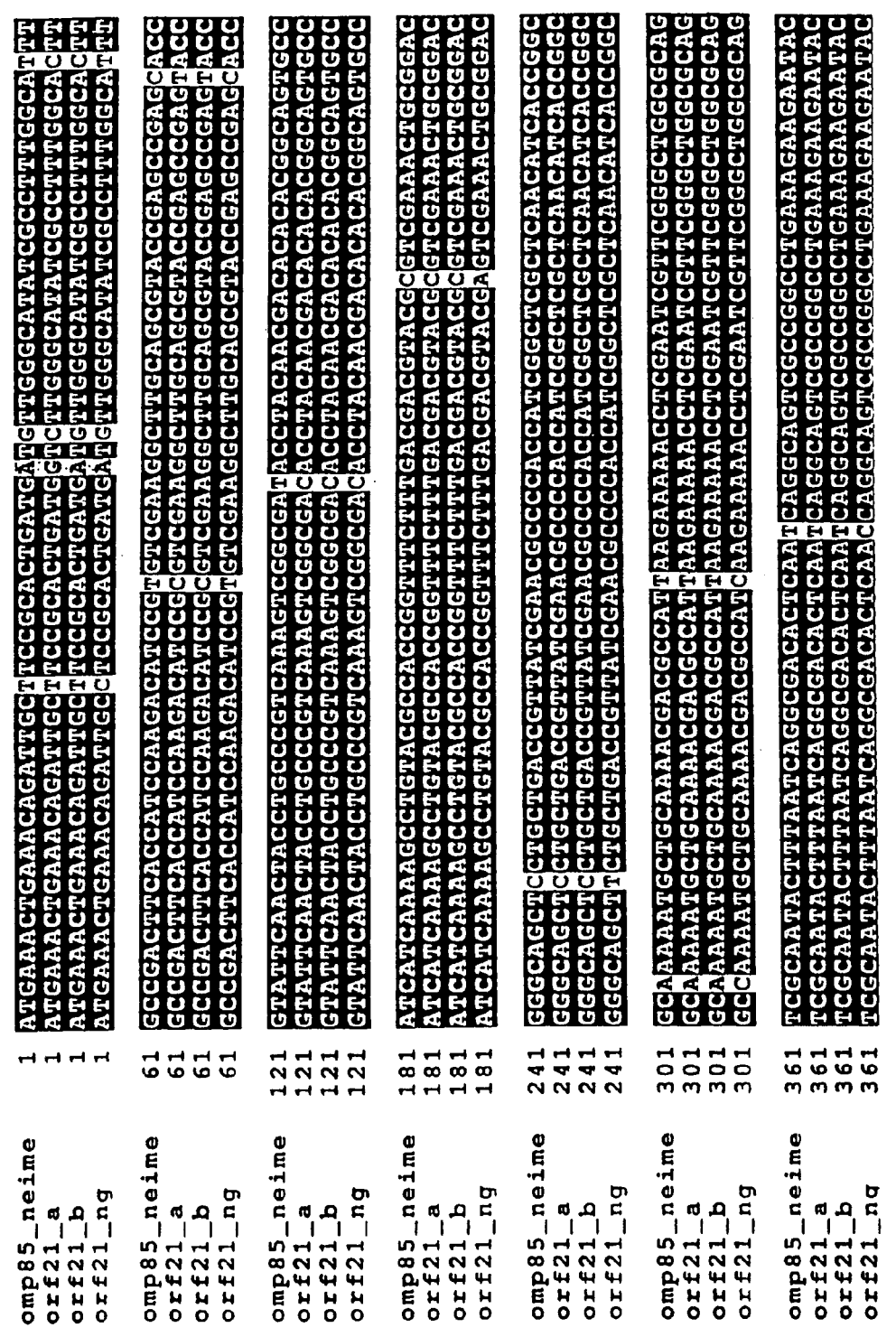
Figure 2:
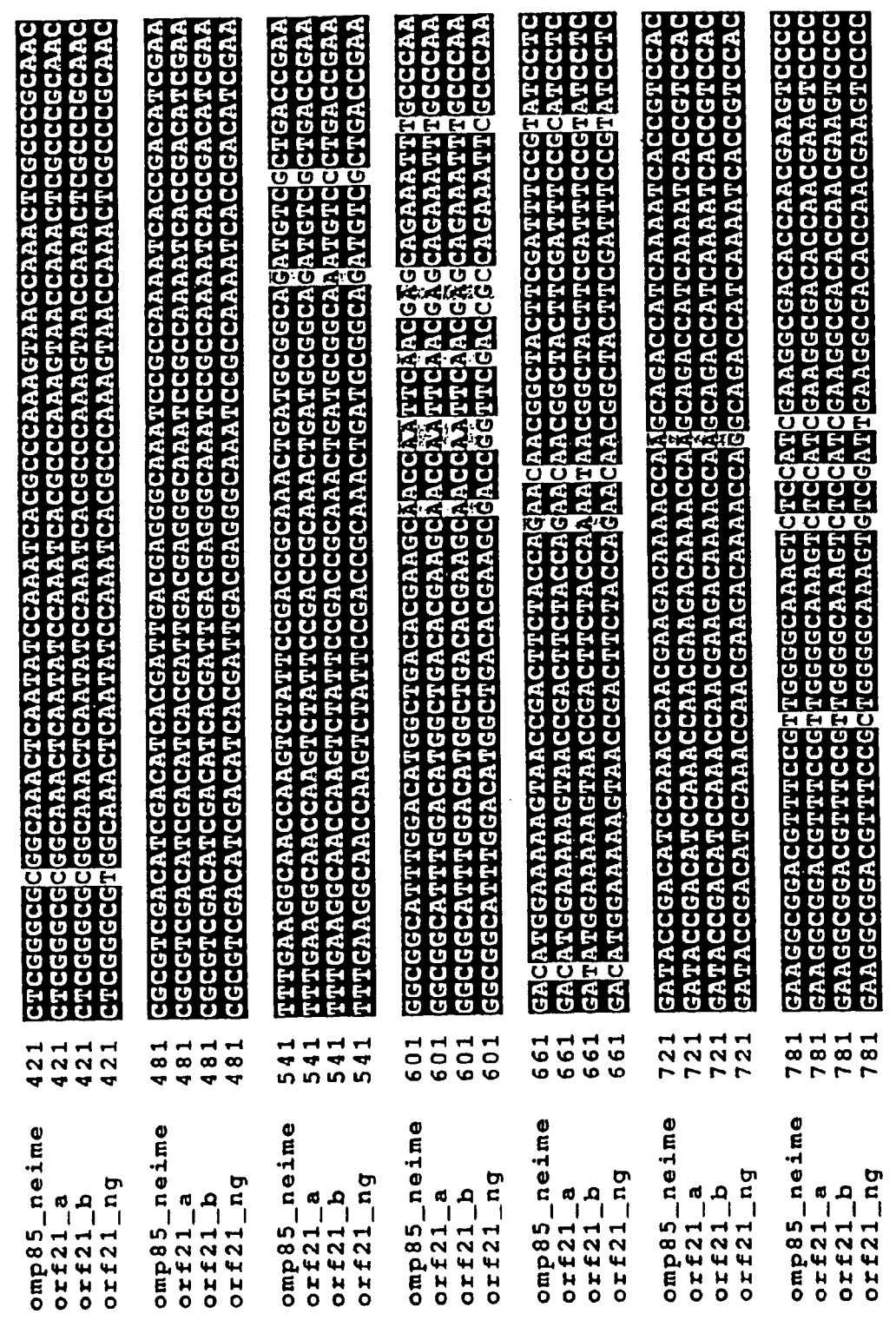
Figure 2:
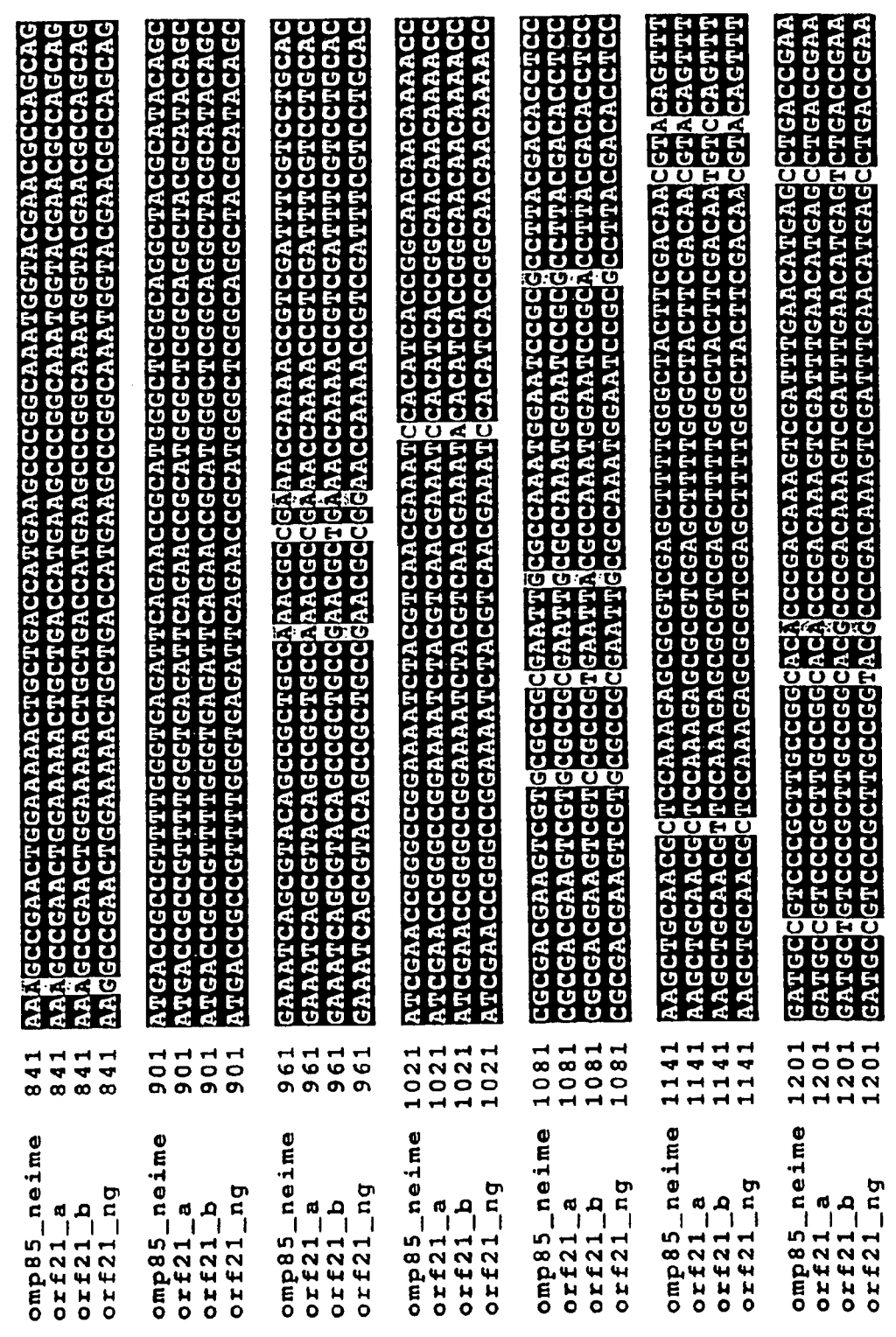
Figure 2:
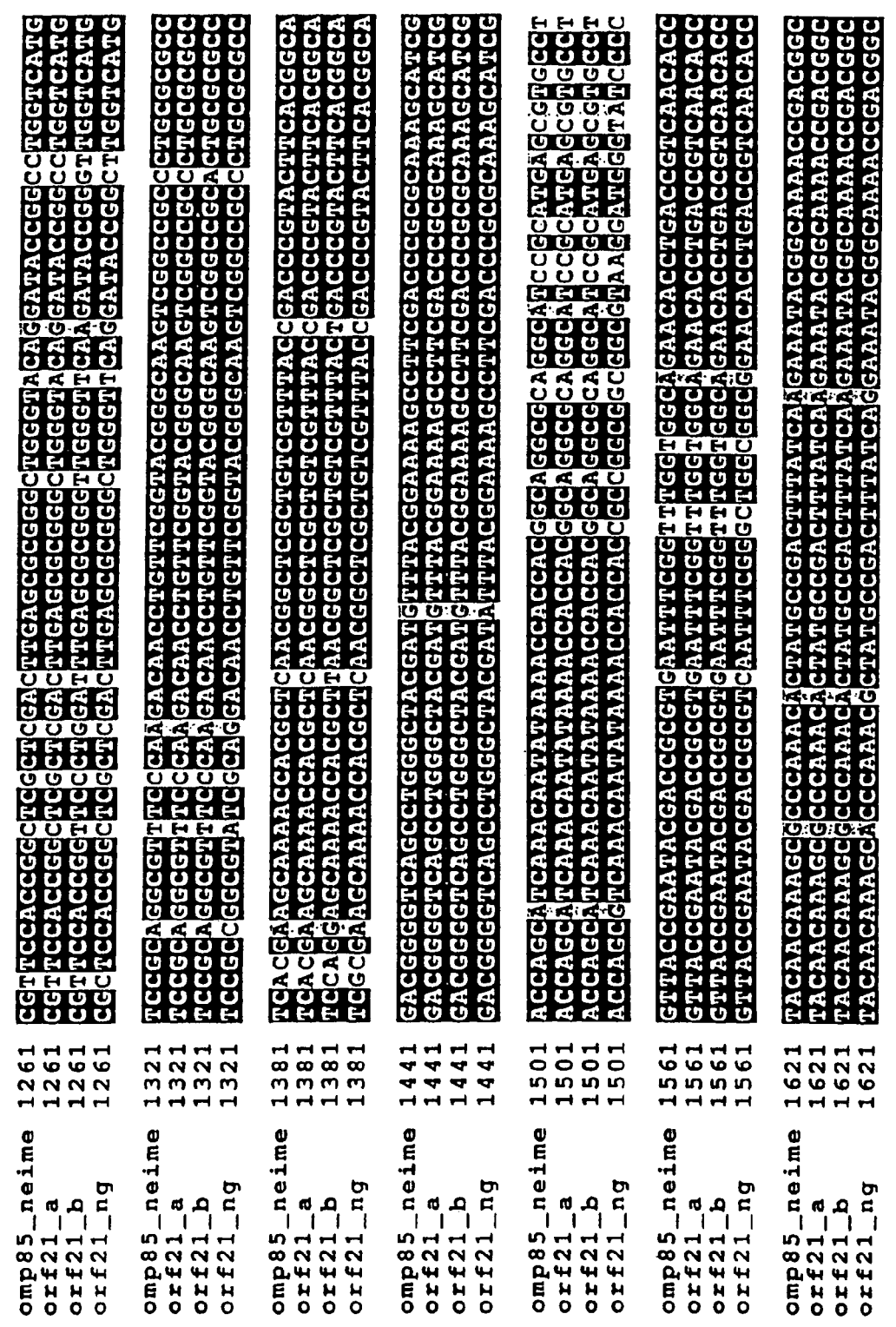
Figure 2:
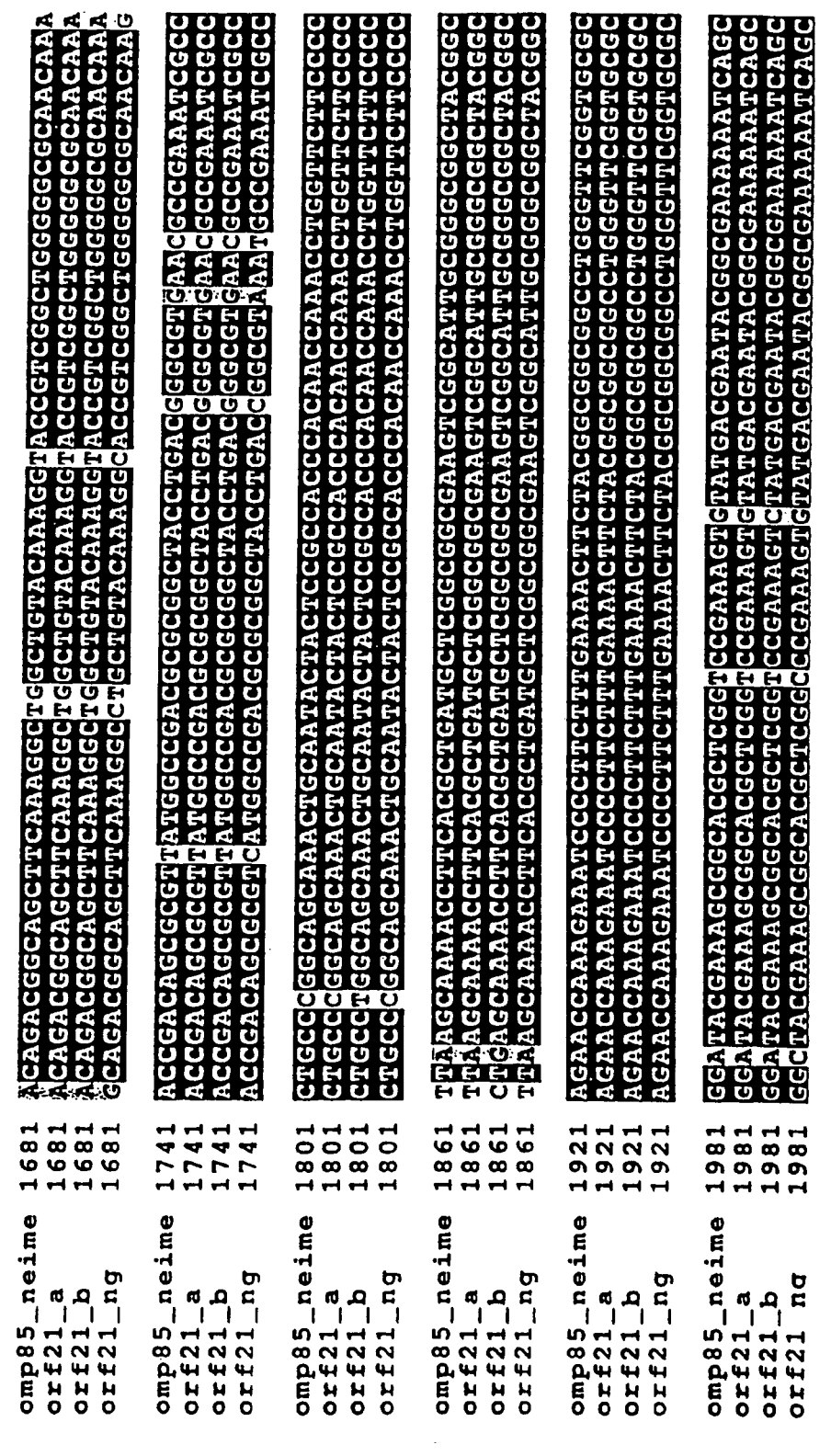

FIG. 2 shows an alignment of ORF21 sequences from MenA (orf21_a), MenB (orf21_b), and gonococcus (orf21_ng) with Omp85 (omp85_neime).

DISCLOSURE OF THE INVENTION

Proteins

The invention provides a protein comprising one or more of the following amino acid sequences: SEQ ID 1, SEQ ID 3, SEQ ID 4, SEQ ID 5, SEQ ID 7, SEQ ID 8, SEQ ID 9, SEQ ID 11, SEQ ID 12, SEQ ID 13.

It also provides a protein comprising a sequence having sequence identity to SEQ ID 1, SEQ ID 3, SEQ ID 4, SEQ ID 5, SEQ ID 7, SEQ ID 8, SEQ ID 9, SEQ ID 11, SEQ ID 12, or SEQ ID 13. Depending on the particular SEQ ID, the degree of sequence identity is preferably greater than 50% (e.g. 60%, 70%, 80%, 90%, 95%, 99% or more). These homologous sequences include mutants and allelic variants. Typically, 50% identity or more between two proteins is considered to be an indication of functional equivalence. Identity between proteins is preferably determined by the Smith-Waterman homology search algorithm as implemented in the MPSRCH program (Oxford Molecular), using an affine gap search with parameters gap open penalty=12 and gap extension penalty=1.

The invention further provides a protein comprising a fragment of SEQ ID 1, SEQ ID 3, SEQ ID 4, SEQ ID 5, SEQ ID 7, SEQ ID 8, SEQ ID 9, SEQ ID 11, SEQ ID 12, or SEQ ID 13. The fragment should comprise at least n consecutive amino acids from the sequence and, depending on the particular sequence, n is 7 or more (e.g. 8, 10, 12, 14, 16, 18, 20 or more). Preferably the fragment comprises an epitope from the sequence.

The proteins of the invention can, of course, be prepared by various means (e.g. recombinant expression, purification from cell culture, chemical synthesis etc.) and in various forms (e.g. native, fusions etc.). They are preferably prepared in substantially pure form (i.e. substantially free from other *Neisseria* or host cell proteins).

Antibodies

According to a further aspect, the invention provides antibodies which bind to these proteins. These may be polyclonal or monoclonal and may be produced by any suitable means.

Nucleic Acids

According to a further aspect, the invention provides nucleic acid comprising SEQ ID 2, SEQ ID 6, or SEQ ID 10. In addition, the invention provides nucleic acid comprising sequences having sequence identity to SEQ ID 2, SEQ ID 6, or SEQ ID 10. Depending on the particular SEQ ID, the degree of sequence identity is preferably greater than 50% (e.g. 60%, 70%, 80%, 90%, 95%, 99% or more). Sequence identity is preferably determined by the Smith-Waterman homology search algorithm as implemented in the MPSRCH program (Oxford Molecular), using an affine gap search with parameters gap open penalty=12 and gap extension penalty=1.

Furthermore, the invention provides nucleic acid which can hybridise to SEQ ID 2, SEQ ID 6, or SEQ ID 10, preferably under "high stringency" conditions (e.g. 65° C. in a 0.1×SSC, 0.5% SDS solution).

Nucleic acid comprising fragments of SEQ ID 2, SEQ ID 6, or SEQ ID 10 are also provided. These should comprise at least n consecutive nucleotides from SEQ ID 2, SEQ ID 6, or SEQ ID 10 and, depending on the particular sequence, n is 10 or more (eg 12, 14, 15, 18, 20, 25, 30, 35, 40 or more).

According to a further aspect, the invention provides nucleic acid encoding the proteins and protein fragments of the invention.

It should also be appreciated that the invention provides nucleic acid comprising sequences complementary to those described above (e.g. for antisense or probing purposes).

Nucleic acid according to the invention can, of course, be prepared in many ways (e.g. by chemical synthesis, from genomic or cDNA libraries, from the organism itself etc.) and can take various forms (e.g. single stranded, double stranded, vectors, probes etc.).

In addition, the term "nucleic acid" includes DNA and RNA, and also their analogues, such as those containing modified backbones, and also peptide nucleic acids (PNA) etc.

According to a further aspect, the invention provides vectors comprising nucleotide sequences of the invention (e.g. expression vectors) and host cells transformed with such vectors.

Compositions

According to a further aspect, the invention provides compositions comprising protein, antibody, and/or nucleic acid according to the invention. These compositions may be suitable as vaccines, for instance, or as diagnostic reagents, or as immunogenic compositions.

The compositions of the invention may further comprise immunogenic components selected from one or more of the following:

the proteins disclosed in WO99/57280 or immunogenic fragments thereof;
the proteins disclosed in WO99/36544 or immunogenic fragments thereof;
the proteins disclosed in WO99/24578 or immunogenic fragments thereof;
the proteins disclosed in Tettelin et al. [*Science* (2000) 287:1809-1815; NMB0001 to NMB2160] or immunogenic fragments thereof;
the proteins disclosed in WO97/28273 or immunogenic fragments thereof;
the proteins disclosed in WO96/29412 or immunogenic fragments thereof;
the proteins disclosed in WO95/03413 or immunogenic fragments thereof;
the proteins disclosed in WO99/31132 or immunogenic fragments thereof;
a protective antigen against *Neisseria meningitidis* serogroup A;
a protective antigen against *Neisseria meningitidis* serogroup C;
a protective antigen against *Neisseria meningitidis* serogroup Y;
a protective antigen against *Neisseria meningitidis* serogroup W;
a protective antigen against *Haemophilus influenzae;*
a protective antigen against pneumococcus;
a protective antigen against diphtheria;
a protective antigen against tetanus;
a protective antigen against whooping cough;
a protective antigen against *Helicobacter pylori;*
a protective antigen against polio; and/or
a protective antigen against hepatitis B virus.

Preferably, the compositions further comprise immunogenic components selected from one or more of the following:

a protein comprising an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, & 892, as disclosed in WO99/24578 (or a protein comprising an immunogenic fragment of one or more of these SEQ IDs, or a protein comprising a sequence having sequence identity (preferably greater than 50% e.g. 60%, 70%, 80%, 90%, 95%, 99% or more) to one of these SEQ IDs);

a protein comprising an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, & 90, as disclosed in WO99/36544 (or a protein comprising an immunogenic fragment of one or more of these SEQ IDs, or a protein comprising a sequence having sequence identity (preferably greater than 50% e.g. 60%, 70%, 80%, 90%, 95%, 99% or more) to one of these SEQ IDs);

a protein encoded by one of the 2160 genes NMB0001 to NMB2160 disclosed in Tettelin et al. [*Science* (2000) 287:1809-1815] (or a protein comprising an immunogenic fragment of one or more of these 2160 genes, or a protein comprising a sequence having sequence identity (preferably greater than 50% e.g. 60%, 70%, 80%, 90%, 95%, 99% or more) to one of these 2160 genes);

a protein comprising an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, 1164, 1166, 1168, 1170, 1172, 1174, 1176, 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, 1300, 1302, 1304, 1306, 1308, 1310, 1312, 1314, 1316, 1318, 1320, 1322, 1324, 1326, 1328, 1330, 1332, 1334, 1336, 1338, 1340, 1342, 1344, 1346, 1348, 1350, 1352, 1354, 1356, 1358, 1360, 1362, 1364, 1366, 1368, 1370, 1372, 1374, 1376, 1378, 1380, 1382, 1384, 1386, 1388, 1390, 1392, 1394, 1396, 1398, 1400, 1402, 1404, 1406, 1408, 1410, 1412, 1414, 1416, 1418, 1420, 1422, 1424, 1426, 1428, 1430, 1432, 1434, 1436, 1438, 1440, 1442, 1444, 1446, 1448, 1450, 1452, 1454, 1456, 1458, 1460, 1462, 1464, 1466, 1468, 1470, 1472, 1474, 1476, 1478, 1480, 1482, 1484, 1486, 1488, 1490, 1492, 1494, 1496, 1498, 1500, 1502, 1504, 1506, 1508, 1510, 1512, 1514, 1516, 1518, 1520, 1522, 1524, 1526, 1528, 1530, 1532, 1534, 1536, 1538, 1540, 1542, 1544, 1546, 1548, 1550, 1552, 1554, 1556, 1558, 1560, 1562, 1564, 1566, 1568, 1570, 1572, 1574, 1576, 1578, 1580, 1582, 1584, 1586, 1588, 1590, 1592, 1594, 1596, 1598, 1600, 1602, 1604, 1606, 1608, 1610, 1612, 1614, 1616, 1618, 1620, 1622, 1624, 1626, 1628, 1630, 1632, 1634, 1636, 1638, 1640, 1642, 1644, 1646, 1648, 1650, 1652, 1654, 1656, 1658, 1660, 1662, 1664, 1666, 1668, 1670, 1672, 1674, 1676, 1678, 1680, 1682, 1684, 1686, 1688, 1690, 1692, 1694, 1696, 1698, 1700, 1702, 1704, 1706, 1708, 1710, 1712, 1714, 1716, 1718, 1720, 1722, 1724, 1726, 1728, 1730, 1732, 1734, 1736, 1738, 1740, 1742, 1744, 1746, 1748, 1750, 1752, 1754, 1756, 1758, 1760, 1762, 1764, 1766, 1768, 1770, 1772, 1774, 1776, 1778, 1780, 1782, 1784, 1786, 1788, 1790, 1792, 1794, 1796, 1798, 1800, 1802, 1804, 1806, 1808, 1810, 1812, 1814, 1816, 1818, 1820, 1822, 1824, 1826, 1828, 1830, 1832, 1834, 1836, 1838, 1840, 1842, 1844, 1846, 1848, 1850, 1852, 1854, 1856, 1858, 1860, 1862, 1864, 1866, 1868, 1870, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2030, 2032, 2034, 2036, 2038, 2040, 2042, 2044, 2046, 2048, 2050, 2052, 2054, 2056, 2058, 2060, 2062, 2064, 2066, 2068, 2070, 2072, 2074, 2076, 2078, 2080, 2082, 2084, 2086, 2088, 2090, 2092, 2094, 2096, 2098, 2100, 2102, 2104, 2106, 2108, 2110, 2112, 2114, 2116, 2118, 2120, 2122, 2124, 2126, 2128, 2130, 2132, 2134, 2136, 2138, 2140, 2142, 2144, 2146, 2148, 2150, 2152, 2154, 2156, 2158, 2160, 2162, 2164, 2166, 2168, 2170, 2172, 2174, 2176, 2178, 2180, 2182, 2184, 2186, 2188, 2190, 2192, 2194, 2196, 2198, 2200, 2202, 2204, 2206, 2208, 2210, 2212, 2214, 2216, 2218, 2220, 2222, 2224, 2226, 2228, 2230, 2232, 2234, 2236, 2238, 2240, 2242, 2244, 2246, 2248, 2250, 2252, 2254, 2256, 2258, 2260, 2262, 2264, 2266, 2268, 2270, 2272, 2274, 2276, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2324, 2326, 2328, 2330, 2332, 2334, 2336, 2338, 2340, 2342, 2344, 2346, 2348, 2350, 2352, 2354, 2356, 2358, 2360, 2362, 2364, 2366, 2368, 2370, 2372, 2374, 2376, 2378, 2380, 2382, 2384, 2386, 2388, 2390, 2392, 2394, 2396, 2398, 2400, 2402, 2404, 2406, 2408, 2410, 2412, 2414, 2416, 2418, 2420, 2422, 2424, 2426, 2428, 2430, 2432, 2434, 2436, 2438, 2440, 2442, 2444, 2446, 2448, 2450, 2452, 2454, 2456, 2458, 2460, 2462, 2464, 2466, 2468, 2470, 2472, 2474, 2476, 2478, 2480, 2482, 2484, 2486, 2488, 2490, 2492, 2494, 2496, 2498, 2500, 2502, 2504, 2506, 2508, 2510, 2512, 2514, 2516, 2518, 2520, 2522, 2524, 2526, 2528, 2530, 2532, 2534, 2536, 2538, 2540, 2542, 2544, 2546, 2548, 2550, 2552, 2554, 2556, 2558, 2560, 2562, 2564, 2566, 2568, 2570, 2572, 2574, 2576, 2578, 2580, 2582, 2584, 2586, 2588, 2590, 2592, 2594, 2596, 2598, 2600, 2602, 2604, 2606, 2608, 2610, 2612, 2614, 2616, 2618, 2620, 2622, 2624, 2626, 2628, 2630, 2632, 2634, 2636, 2638, 2640, 2642, 2644, 2646, 2648, 2650, 2652, 2654, 2656, 2658, 2660, 2662, 2664, 2666, 2668, 2670, 2672, 2674, 2676, 2678, 2680, 2682, 2684, 2686, 2688, 2690, 2692, 2694, 2696, 2698, 2700, 2702, 2704, 2706, 2708, 2710, 2712, 2714, 2716, 2718, 2720, 2722, 2724, 2726, 2728, 2730, 2732, 2734, 2736, 2738, 2740, 2742, 2744, 2746, 2748, 2750, 2752, 2754, 2756, 2758, 2760, 2762, 2764, 2766, 2768, 2770, 2772, 2774, 2776, 2778, 2780, 2782, 2784, 2786, 2788, 2790, 2792, 2794, 2796, 2798, 2800, 2802, 2804, 2806, 2808, 2810, 2812, 2814, 2816, 2818, 2820, 2822, 2824, 2826, 2828, 2830, 2832, 2834, 2836, 2838, 2840, 2842, 2844, 2846, 2848, 2850, 2852, 2854, 2856, 2858, 2860, 2862, 2864, 2866, 2868, 2870, 2872, 2874, 2876, 2878, 2880, 2882, 2884, 2886, 2888, 2890, 2892, 2894, 2896, 2898, 2900, 2902, 2904, 2906, 2908, 2910, 2912, 2914, 2916, 2918, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964, 2966, 2968, 2970, 2972, 2974, 2976, 2978, 2980, 2982, 2984, 2986, 2988, 2990, 2992, 2994, 2996, 2998, 3000, 3002, 3004, 3006, 3008, 3010, 3012, 3014, 3016, 3018 & 3020, as disclosed in WO99/57280 (or a protein comprising an immunogenic fragment of one or more of these SEQ IDs, or a protein comprising a sequence having sequence identity (preferably greater than 50% e.g. 60%, 70%, 80%, 90%, 95%, 99% or more) to one of these SEQ IDs);

The protein disclosed in FIG. 4 or FIG. 13 of WO97/28273;

A protein comprising an amino acid sequence selected from the group consisting of SEQ IDs 1-8 disclosed in WO96/29412 (or a protein comprising an immunogenic fragment of one or more of these SEQ IDs, or a protein comprising a sequence having sequence identity (preferably greater than 50% e.g. 60%, 70%, 80%, 90%, 95%, 99% or more) to one of these SEQ IDs);

A protein comprising an amino acid sequence selected from the group consisting of SEQ IDs 1-23 disclosed in WO95/03413 (or a protein comprising an immunogenic fragment of one or more of these SEQ IDs, or a protein comprising a sequence having sequence identity (preferably greater than 50% e.g. 60%, 70%, 80%, 90%, 95%, 99% or more) to one of these SEQ IDs);

A protein comprising an amino acid sequence consisting of SEQ ID 2 disclosed in WO99/31132 (or a protein comprising an immunogenic fragment of SEQ ID 2, or a protein comprising a sequence having sequence identity (preferably greater than 50% e.g. 60%, 70%, 80%, 90%, 95%, 99% or more) to SEQ ID 2);

A polysaccharide antigen against *Neisseria meningitidis* serogroup A;

A polysaccharide antigen against *Neisseria meningitidis* serogroup C, such as that described in Costantino et al. (1992) *Vaccine* 10:691-698;

A polysaccharide antigen against *Neisseria meningitidis* serogroup Y;

A polysaccharide antigen against *Neisseria meningitidis* serogroup W;

A polysaccharide antigen against *Haemophilus influenzae*;

A polysaccharide antigen against pneumococcus;

A protective antigen against diphtheria, consisting of a diphtheria toxoid, such as the CRM197 mutant [e.g. Del Guidice et al. (1998) *Molecular Aspects of Medicine* 19:1-70].

A protective antigen against tetanus, consisting of a tetanus toxoid [e.g. Wassilak & Orenstein, Chapter 4 of *Vaccines* (eds. Plotkin & Mortimer), 1988]

A protective antigen against whooping cough, comprising pertussis holotoxin (PT) and filamentous haemagglutinin (FHA); optionally further comprising pertactin and/or agglutinogens 2 and 3 [e.g. Gustafsson et al. (1996) *N. Engl. J. Med.* 334:349-355; Rappuoli et al. (1991) *TIBTECH* 9:232-238].

A protective antigen against *H. pylori*, comprising one or more of CagA (e.g. WO93/18150), VacA (e.g. WO93/18150), NAP (e.g. WO99/53310), HopX (e.g. WO98/04702), HopY (e.g. WO98/04702), urease.

A protective antigen against hepatitis B virus, consisting of a HBV surface antigen and/or a HBV core antigen.

Where the composition comprises an antigen against diphtheria, it preferably also comprises antigens against tetanus and polio. Where the composition comprises an antigen against tetanus, it preferably also comprises antigens against diphtheria and polio. Where the composition comprises an antigen against polio, it preferably also comprises antigens against diphtheria and tetanus.

Pertussis toxin is a toxic protein and, when present in the composition, it is preferably detoxified. Detoxification may be by chemical and/or genetic means. A preferred detoxified mutant is the 9K/129G double mutant [e.g. Rappuoli (1997) *Nature Medicine* 3:374-376].

Where the composition includes a protein that exists in different nascent and mature forms, the mature form of the protein is preferably used. For example, where NspA is included, (WO96/29412; see also Martin et al. (1997) *J. Exp. Med* 185 1173-1183) the mature form of the protein lacking the signal peptide is preferably used.

Where the composition includes a polysaccharide antigen, the polysaccharide is preferably conjugated to a carrier protein.

The proteins of the invention present in the compositions preferably interact synergistically with at least one of the protective antigens in the composition.

Therapy, Prophylaxis, Diagnosis

The invention also provides the compositions of the invention for use as medicaments (preferably as vaccines) or as diagnostic reagents. It also provides the use of a composition according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. Said Neisserial bacteria may be any species or strain (such as *N. gonorrhoeae*) but are preferably *N. meningitidis*, especially serogroup B.

The invention also provides a method of treating a patient, comprising administering to the patient a therapeutically effective amount of nucleic acid, protein, and/or antibody according to the invention. The method is preferably immunisation.

Vaccines according to the invention may either be prophylactic (i.e. to prevent infection) or therapeutic (i.e. to treat disease after infection).

Processes

According to further aspects, the invention provides various processes.

A process for producing proteins of the invention is provided, comprising the step of culturing a host cell according to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridizing conditions to form duplexes; and (b) detecting said duplexes.

A process for detecting proteins of the invention is provided, comprising the steps of: (a) contacting an antibody according to the invention with a biological sample under conditions suitable for the formation of an antibody-antigen complexes; and (b) detecting said complexes.

MODES FOR CARRYING OUT THE INVENTION

A summary of standard techniques and procedures which may be employed in order to perform the invention (e.g. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature e.g. Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g. a composition "comprising" X may consist exclusively of X or may include something additional to X, such as X+Y.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a Neisserial sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

A "mutant" sequence is defined as DNA, RNA or amino acid sequence differing from but having sequence identity with the native or disclosed sequence. Depending on the particular sequence, the degree of sequence identity between the native or disclosed sequence and the mutant sequence is preferably greater than 50% (e.g. 60%, 70%, 80%, 90%, 95%, 99% or more, calculated using the Smith-Waterman algorithm as described above). As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (e.g. see U.S. Pat. No. 5,753, 235).

Expression Systems

The Neisserial nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual*, 2nd ed.].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual*].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No. 1555* (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA*, 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g. Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g. HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*, Malcolm B. Wilkins, ed., 1984 Pitman Publishing Limited, London, pp. 21-52. References that describe other metabolically-regulated genes: Sheen, *Plant Cell,* 2:1027-1038(1990); Maas et al., *EMBO J.* 9:3447-3452 (1990); Benkel and Hickey, *Proc. Natl. Acad. Sci.* 84:1337-1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes.

Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet,* 202:179-185, 1985. The genetic material may also be transferred into the plant cell by using polyethylene glycol, Krens, et al., *Nature,* 296, 72-74, 1982. Another method of introduction of nucleic acid segments is high velocity ballistic penetration by small particles with the nucleic acid either within the matrix of small beads or particles, or on the surface, Klein, et al., *Nature,* 327, 70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA,* 79, 1859-1863, 1982.

The vector may also be introduced into the plant cells by electroporation. (Fromm et al., *Proc. Natl. Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum,* and *Datura.*

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli (E. coli)* [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In Interferon 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual]*.

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) J. Biotechnol. 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g. [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus* lactis by electroporation, in: Streptococcal Genetics (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g. EP-A-0 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (e.g. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (e.g. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) Gene 8:17-24], pCl/1 [Brake et al. (1984) Proc. Natl. Acad. Sci USA 81:4642-4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) Proc. Natl. Acad. Sci. USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol, Rev. 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans [Kurtz, et al. (1986) Mol. Cell. Biol. 6:142], Candida maltosa [Kunze, et al. (1985) J. Basic Microbiol. 25:141]. Hansenula polymorpha [Gleeson, et al. (1986) J. Gen. Microbiol. 132:3459; Roggenkamp et al. (1986) Mol. Gen. Genet. 202:302], Kluyveromyces fragilis [Das, et al. (1984) J. Bacteriol. 158:1165], Kluyveromyces lactis [De Louvencourt et al. (1983) J. Bacteriol. 154:737; Van den Berg et al. (1990) Bio/Technology 8:135], Pichia guillerimondii [Kunze et al. (1985) J. Basic Microbiol. 25:141], Pichia pastoris [Cregg, et al. (1985) Mol. Cell. Biol. 5:3376; U.S. Pat. Nos. 4,837,148 and 4,929,555], Saccharomyces cerevisiae [Hinnen et al. (1978) Proc. Natl. Acad. Sci. USA 75:1929; Ito et al. (1983) J. Bacteriol. 153:163], Schizosaccharomyces pombe [Beach and Nurse (1981) Nature 300:706], and Yarrowia lipolytica [Davidow, et al. (1985) Curr. Genet. 10:380471 Gaillardin, et al. (1985) Curr. Genet. 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g. [Kurtz et al. (1986) Mol. Cell. Biol. 6:142; Kunze et al. (1985) J. Basic Microbiol. 25:141; Candida]; [Gleeson et al. (1986) J. Gen. Microbiol. 132:3459; Roggenkamp et al. (1986) Mol. Gen. Genet. 202:302; Hansenula]; [Das et al. (1984) J. Bacteriol. 158:1165; De Louvencourt et al. (1983) J. Bacteriol. 154: 1165; Van den Berg et al. (1990) Bio/Technology 8:135; Kluyveromyces]; [Cregg et al. (1985) Mol. Cell. Biol. 5:3376; Kunze et al. (1985) J. Basic Microbiol. 25:141; U.S. Pat. Nos. 4,837,148 and 4,929,555; Pichia]; [Hinnen et al. (1978) Proc. Natl. Acad. Sci. USA 75; 1929; Ito et al. (1983) J. Bacteriol. 153:163 Saccharomyces]; [Beach and Nurse (1981) Nature 300:706; Schizosaccharomyces]; [Davidow et al. (1985) Curr. Genet. 10:39; Gaillardin et al. (1985) Curr. Genet. 10:49; Yarrowia].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying Neisserial proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (e.g. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g. hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (e.g. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g. see WO98/20734), needles, and gene guns or hyposprays. Dosage treatment may be a single dose schedule or a multiple dose schedule.

Vaccines

Vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12, etc.), interferons (e.g. gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (e.g. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g. by injection, either subcutaneously, intramuscularly, or transdermally/transcutaneously (e.g. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be employed [e.g. Robinson & Torres (1997) *Seminars in Immunology* 9:271-283; Donnelly et al. (1997) *Annu Rev Immunol* 15:617-648; see later herein].

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) Biochim. Biophys. Acta. 1097:1-17; Straubinger (1983) Meth. Enzymol. 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) Proc. Natl. Acad. Sci. USA 84:7413-7416); mRNA (Malone (1989) Proc. Natl. Acad. Sci. USA 86:6077-6081); and purified transcription factors (Debs (1990) J. Biol. Chem. 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, e.g. Szoka (1978) Proc. Natl. Acad. Sci. USA 75:4194-4198; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See e.g. Straubinger (1983) Meth. Immunol. 101:512-527; Szoka (1978) Proc. Natl. Acad. Sci. USA 75:4194-4198; Papahadjopoulos (1975) Biochim. Biophys. Acta 394:483; Wilson (1979) Cell 17:77); Deamer & Bangham (1976) Biochim. Biophys. Acta 443:629; Ostro (1977) Biochem. Biophys. Res. Commun. 76:836; Fraley (1979) Proc. Natl. Acad. Sci. USA 76:3348); Enoch & Strittmatter (1979) Proc. Natl. Acad. Sci. USA 76:145; Fraley (1980) J. Biol. Chem. (1980) 255:10431; Szoka & Papahadjopoulos (1978) Proc. Natl. Acad. Sci. USA 75:145; and Schaefer-Ridder (1982) Science 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acid of these apoproteins are known and are described in, for example, Breslow (1985) Annu Rev. Biochem 54:699; Law (1986) Adv. Exp Med. Biol. 151:162; Chen (1986) J Biol Chem 261:12918; Kane (1980) Proc Natl Acad Sci USA 77:2465; and Utermann (1984) Hum Genet 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in Meth. Enzymol. 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in Meth. Enzymol. (supra); Pitas (1980) J. Biochem. 255:5454-5460 and Mahey (1979) J. Clin. Invest 64:743-750. Lipoproteins can also be produced by in vitro or recombinant methods by expression of the apoprotein genes in a desired host cell. See, for example, Atkinson (1986) Annu Rev Biophys Chem 15:403 and Radding (1958) Biochim Biophys Acta 30: 443. Lipoproteins can also be purchased from commercial suppliers, such as Biomedical Techniologies, Inc., Stoughton, Mass., USA. Further description of lipoproteins can be found in Zuckermann et al. PCT/US97/14465.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10} Ci)+0.4[\%(G+C)]-0.6(\%\text{formamide})-600/n-1.5(\%\text{mismatch}).$$

where Ci is the salt concentration (monovalent ions) and n is the length of the hybrid in base pairs (slightly modified from Meinkoth & Wahl (1984) Anal. Biochem. 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

MODES FOR CARRYING OUT THE INVENTION

Identification of the Meningococcal 80-85 kDa Protein

It was observed that various outer membrane vesicle preparations from N. meningitidis serogroup B contained a component of approximately 80-85 kDa. This protein was purified from SDS-PAGE gels and N-terminal sequenced (SEQ ID 1).

Antibodies raised against the SDS-PAGE purified protein cross-reacted with equivalent proteins in more than 50 N. meningitidis strains of diverse serogroups and serotypes. Cross-reactivity with N. gonorrhoeae, N. polysaccharia and N. lactamica was also observed. Post-immune sera from vaccinated patients also reacted with the protein.

The complete gene was cloned from serogroup B N. meningitidis (SEQ ID 2) and the encoded protein was inferred (SEQ ID 3). By comparison with the N-terminal sequencing described above, a signal peptide (SEQ ID 4) and a mature sequence (SEQ ID 5) are inferred.

Identification of Corresponding Genes in *N. meningitidis* Serogroup a and *N. gonorrhoeae*

On the basis of the serogroup B *N. meningitidis* sequence, the corresponding genes from *N. meningitidis* serogroup A and *N. gonorrhoeae* were cloned and sequenced (called 'ORF21').

The complete gene from serogroup A *N. meningitidis* is shown in SEQ ID 6, with the encoded protein in SEQ ID 7. The signal peptide and mature sequence are SEQ IDs 8 and 9.

The complete gene from *N. gonorrhoeae* is shown in SEQ ID 10, with the encoded protein in SEQ ID 11. The signal peptide and mature sequence are SEQ IDs 12 and 13.

Sequence Comparisons

The protein sequences were compared and are highly homologous.

The *N. meningitidis* serogroup B sequence and the *N. gonorrhoeae* sequence show 95.4% identity in 797 aa overlap:

```
                      10         20         30         40         50         60
orf21.pep     MKLKQIASALMMLGISPLALADFTIQDIRVEGLQRTEPSTVFNYLPVKVGDTYNDTHGSA
              ||||||||||||||||||||:|||||||||||||||||||||||||||||||||||||||
orf21ng.pep   MKLKQIASALMMLGISPLAFADFTIQDIRVEGLQRTEPSTVFNYLPVKVGDTYNDTHGSA
                      10         20         30         40         50         60

70         80         90        100        110        120
orf21.pep     IIKSLYATGFFDDVRVETADGQLLLTVIERPTIGSLNITGAKMLQNDAIKKNLESFGLAQ
              ||||||||||||||||||||||||||||||||||||||||||||||||||||||||||||
orf21ng.pep   IIKSLYATGFFDDVRVETADGQLLLTVIERPTIGSLNITGAKMLQNDAIKKNLESFGLAQ
                      70         80         90        100        110        120

130        140        150        160        170        180
orf21.pep     SQYFNQATLNQAVAGLKEEYLGRGKLNIQITPKVTKLARNRVDIDITIDEGKSAKITDIE
              ||||||||||||||||||||||||||||||||||||||||||||||||||||||||||||
orf21ng.pep   SQYFNQATLNQAVAGLKEEYLGRGKLNIQITPKVTKLARNRVDIDITIDEGKSAKITDIE
                     130        140        150        160        170        180

190        200        210        220        230        240
orf21.pep     FEGNQVYSDRKLMRQMSLTEGGIWTWLTRSNQFNEQKFAQDMEKVTDFYQNNGYFDFRIL
              ||||||||||||||||||||||||||||||||::|:::||||||||||||||||||||||
orf21ng.pep   FEGNQVYSDRKLMRQMSLTEGGIWTWLTRSDRFDRQKFAQDMEKVTDFYQNNGYFDFRIL
                     130        200        210        220        230        240

250        260        270        280        290        300
orf21.pep     DTDIQTNEDKTKQTIKITVHEGGRFRQGKVSIEGDTNEVPKAELEKLLTMKPGKWYERQQ
              ||||||||||:|||||||||||||||:|||||||||||||||||||||||||||||||||
orf21ng.pep   DTDIQTNEDKTRQTIKITVHEGGRFRWGKVSIEGDTNEVPKAELEKLLTMKPGKWYERQQ
                     250        260        270        280        290        300

310        320        330        340        350        360
orf21.pep     MTAVLGEIQNRMGSAGYAYSEISVQPLPNAETKTVDFVLHIEPGRKIYVNEIHITGNNKT
              |||||||||||||||||||||||||||||||:||||||||||||||||||||||||||||
orf21ng.pep   MTAVLGEIQNRMGSAGYAYSEISVQPLPNAGTKTVDFVLHIEPGRKIYVNEIHITGNNKT
                     310        320        330        340        350        360

370        380        390        400        410        420
orf21.pep     RDEVVRRELEQMESAPYDTSKLQRSKERVELLGYFDNVQFDAVPLAGTPDKVDLNMSLTE
              ||||||||||:|||||||||||||||||||||||||||||||||||||||||||||||||
orf21ng.pep   RDEVVRRELRQMESAPYDTSKLQRSKERVELLGYFDNVQFDAVPLAGTPDKVDLNMSLTE
                     370        380        390        400        410        420

430        440        450        460        470        480
orf21.pep     RSTGSLDLSAGWVQDTGLVMSAGVSQDNLFGTGKSAALRASRSKTTLNGSLSFTDPYFTA
              ||||||||||||||||||||||||||||||||||||||||||||||||||||||||||||
orf21ng.pep   RSTGSLDLSAGWVQDTGLVMSAGVSQDNLFGTGKSAALRASRSKTTLNGSLSFTDPYFTA
                     430        440        450        460        470        480

490        500        510        520        530        540
orf21.pep     DGVSLGYDVYGKAFDPRKASTSIKQYKTTTAGAGIRMSVPVTEYDRVNFGLVAEHLTVNT
              ||||||||:|||||||||||||:|||||||||:||||:||||||||||||||:|||||||
orf21ng.pep   DGVSLGYDIYGKAFDPRKASTSVKQYKTTTAGGGIRMGIPVTEYDRVNFGLAAEHLTVNT
                     490        500        510        520        530        540

550        560        570        580        590        600
orf21.pep     YNKAPKHYADFIKKYGKTDGTDGSFKGWLYKGTVGWGRNKTDSALWPTRGYLYGVNAEIA
              ||||||:|||||:|||||||:||||||:||||||||||||||||||:|||||||||||||
orf21ng.pep   YNKAPKRYADFIRKYGKTDGADGSFKGLLYKGTVGWGRNKTDSASWPTRGYLYGVNAEIA
                     550        560        570        580        590        600

610        620        630        640        650        660
orf21.pep     LPGSKLQYYSATHNQTWFFPLSKTFTLMLGGEVGIAGGYGRTKEIPFFENFYGGGLGSVR
              ||||||||||||||||||||||||||||||||||||||||||||||||||||||||||||
orf21ng.pep   LPGSKLQYYSATHNQTWFFPLSKTFTLMLGGEVGIAGGYGRTKEIPFFENFYGGGLGSVR
                     610        620        630        640        650        660

670        680        690        700        710        720
orf21.pep     GYESGTLGPKVYDEYGEKISYGGNKKANVSAELLFPMPGAKDARTVRLSLFADAGSVWDG
              ||||||||||||||||||||||||||||||||||||||||||||||||||||||||||||
orf21ng.pep   GYESGTLGPKVYDEYGEKISYGGNKKANVSAELLFPMPGAKDARTVRLSLFADAGSVWDG
                     670        680        690        700        710        720

730        740        750        760        770        780
orf21.pep     KTYDDNSSSATGGRVQNIYGAGNTHKSTFTNELRYSAFFAVTWLSPLGPMKFSYAYPLKK
              :||    ::|  :|  :::|:    |:|||||||||||||||||||||||||||||||||
orf21ng.pep   RTY----TAAENGNNKSVYSE-NAHKSTFTNELRYSAFFAVTWLSPLGPMKFSYAYPLKK
                                730        740        750        760        770
```

-continued

```
                    790
orf21.pep    KPEDEIQRFQFQLGTTF
             ||||||||||||||||
orf21ng.pep  KPEDEIQRFQFQLGTTFX
              780       790
```

The *N. meningitidis* serogroup A and B sequences show 99.9% identity in 797 aa overlap:

```
                      10        20        30        40        50        60
orf21.pep    MKLKQIASALMMLGISPLALADFTIQDIRVEGLQRTEPSTVFNYLPVKVGDTYNDTHGSA
             |||||||||||:||||||||||||||||||||||||||||||||||||||||||||||||
orf21a.pep   MKLKQIASALMVLGISPLALADFTIQDIRVEGLQRTEPSTVFNYLPVKVGDTYNDTHGSA
                      10        20        30        40        50        60

70        80        90       100       110       120
orf21.pep    IIKSLYATGFFDDVRVETADGQLLLTVIERPTIGSLNITGAKMLQNDAIKKNLESFGLAQ
             |||||||||||:||||||||||||||||||||||||||||||||||||||||||||||||
orf21a.pep   IIKSLYATGFFGGVRVETADGQLLLTVIERPTIGSLNITGAKMLQNDAIKKNLESFGLAQ
                      70        80        90       100       110       120

130       140       150       160       170       180
orf21.pep    SQYFNQATLNQAVAGLKEEYLGRGKLNIQITPKVTKLARNRVDIDITIDEGKSAKITDIE
             ||||||||||||||||||||||||||||||||||||||||||||||||||||||||||||
orf21a.pep   SQYFNQATLNQAVAGLKEEYLGRGKLNIQITPKVTKLARNRVDIDITIDEGKSAKITDIE
                     130       140       150       160       170       180

190       200       210       220       230       240
orf21.pep    FEGNQVYSDRKLMRQMSLTEGGIWTWLTRSNQFNEQKFAQDMEKVTDFYQNNGYFDFRIL
             ||||||||||||||||||||||||||||||:|||||||||||||||||||||||||||||
orf21a.pep   FEGNQVYSDRKLMRQMSLTEEGIWTWLTRSNQKNEQKFAQDMEKVTDFYQNNGYFDFRIL
                     190       200       210       220       230       240

250       260       270       280       290       300
orf21.pep    DTDIQTNEDKTKQTIKITVHEGGRFRWGKVSIEGDTNEVPKAELEKLLTMKPGKWYERQQ
             ||||||||||||||||||||||||||||||||||||||||||||||||||||||||||||
orf21a.pep   DTDIQTNEDKTKQTIKITVHEGGRFRWGKVSIEGDTNEVPKAELEKLLTMKPGKWYERQQ
                     250       260       270       280       290       300

310       320       330       340       350       360
orf21.pep    MTAVLGEIQNRMGSAGYAYSEISVQPLPNAETKTVDFVLHIEPGRKIYBNEIHITGNNKT
             |||||||||||||||||||||||||||||||||||||||||:||||||:|||||||||||
orf21a.pep   MTAVLGEIQNRMGSAGYAYSEISVQPLPNAETKTVDFVLHEIPGRKIYVNEIHITGNNKT
                     310       320       330       340       350       360

370       380       390       400       410       420
orf21.pep    RDEVVRRELRQMESAPYDTSKLQRSKERVELLGYFDNVQFDAVPLAGTPDKVDLNMSLTE
             ||||||||||||||||||||||||||||||||||||||||||||||||||||||||||||
orf21a.pep   RDEVVRRELRQMESAPYDTSKLQRSKERVELLGYFDNVQFDAVPLAGTPDKVDLNMSLTE
                     370       380       390       400       410       420

430       440       450       460       470       480
orf21.pep    RSTGSLDLSAGWVQDTGLVMSAGVSQDNLFGTGKSAALRASRSKTTLNGSLSFTDPYFTA
             ||||||||||||||||||||||||||||||||||||||||||||||||||||||||||||
orf21a.pep   RSTGSLDLSAGWVQDTGLVMSAGVSQDNLFGTGKSAALRASRSKTTLNGSLSFTDPYFTA
                     430       440       450       460       470       480

490       500       510       520       530       540
orf21.pep    DGVSLGYDVYGKAFDPRKASTSIKQYKTTTAGAGIRMSVPVTEYDRVNFGLVAEHLTVNT
             ||||||||||||||||||||||||||||||||||||||||||||||||||||||||||||
orf21a.pep   DGVSLGYDVYGKAFDPRKASTSIKQYKTTTAGAGIRMSVPVTEYDRVNFGLVAEHLTVNT
                     490       500       510       520       530       540

550       560       570       580       590       600
orf21.pep    YNKAPKHYADFIKKYGKTDGTDGSFKGWLYKGTVGWGRNKTDSALWPTRGYLTGVNAEIA
             ||||||||||||||||||||||||||||||||||||||||||||||||||||||||||||
orf21a.pep   YNKAPKHYADFIKKYGKTDGTDGSFKGWLYKGTVGWGRNKTDSALWPTRGYLTGVNAEIA
                     550       560       570       580       590       600

610       620       630       640       650       660
orf21.pep    LPGSKLQYYSATHNQTWFFPLSKTFTLMLGGEVGIAGGYGRTKEIPFFENFYGGGLGSVR
             ||||||||||||||||||||||||||||||||||||||||||||||||||||||||||||
orf21a.pep   LPGSKLQYYSATHNQTWFFPLSKTFTLMLGGEVGIAGGYGRTKEIPFFENFYGGGLGSVR
                     610       620       630       640       650       660

670       680       690       700       710       720
orf21.pep    GYESGTLGPKVYDEYGEKISYGGNKKANVSAELLFPMPGAKDARTVRLSLFADAGSVWDG
             ||||||||||||||||||||||||||||||||||||||||||||||||||||||||||||
orf21a.pep   GYESGTLGPKVYDEYGEKISYGGNKKANVSAELLFPMPGAKDARTVRLSLFADAGSVWDG
                     670       680       690       700       710       720

730       740       750       760       770       780
orf21.pep    KTYDDNSSSATGGRVQNIYGAGNTHKSTFTNELRYSAGGAVTWLSPLGPMKFSYAYPLKK
             ||||||||||||||||||||||||||||||||||||||||||||||||||||||||||||
orf21a.pep   KTYDDNSSSATGGRVQNIYGAGNTHKSTFTNELRYSAGGAVTWLSPLGPMKFSYAYPLKK
                     730       740       750       760       770       780
```

```
                    790
orf21.pep   KPEDEIQRFQFQLGTTF
            ||||||||||||||||
orf21a.pep  KPEDEIQRFQFQLGTTFX
                    790
```

The high degree of conservation suggests that a single protein may be able to induce immune responses against a variety of *Neisseriae* species.

Cloning, Expression and Purification

*N. meningitidis* strains 2996 and MC58 were grown to exponential phase in 100 ml of GC medium, harvested by centrifugation, and resuspended in 5 ml buffer (20% w/v sucrose, 50 mM Tris-HCl, 50 mM EDTA, pH8). After 10 minutes incubation on ice, the bacteria were lysed by adding 10 ml of lysis solution (50 mM NaCl, 1% Na-Sarkosyl, 50 µg/ml Proteinase K), and the suspension incubated at 37° C. for 2 hours. Two phenol extractions (equilibrated to pH 8) and one $CHCl_3$/isoamylalcohol (24:1) extraction were performed. DNA was precipitated by addition of 0.3M sodium acetate and 2 volumes of ethanol, and collected by centrifugation. The pellet was washed once with 70% (v/v) ethanol and redissolved in 4.0 ml TE buffer (10 mM Tris-HCl, 1 mM EDTA, pH 8.0). The DNA concentration was measured by reading $OD_{260}$.

ORF21, without the sequence encoding the leader peptide, was amplified by PCR using the following oligonucleotides:

orf21 for <SEQ ID 105> (BamHI-NdeI)
orf21 rev <SEQ ID 106> (XhoI)

The 5' primer included two restriction sites (BamHI-NdeI), the 3' primer included a XhoI restriction site, in order to direct the cloning of the amplification product (corresponding to ORF21) into the two expression vectors pGEX-KG (using BamHI-XhoI) to have a N-terminal GST-fusion, and pET21b+ (using NdeI-XhoI), to have a C-terminal His-fusion.

The standard PCR protocol was as follows: 200 ng of genomic DNA from 2996 or MC58 strains or 10 ng of plasmid DNA preparation of recombinant clones were used as template in the presence of 40 µM of each oligonucletide primer, 400-800 µM dNTPs solution, 1×PCR buffer (including 1.5 mM $MgCl_2$), 2.5 units TaqI DNA polymerase (using Perkin-Elmer AmpliTaQ, Boerhingher Mannheim Expand™ Long Template).

After a preliminary 3 minute incubation of the whole mix at 95° C., each sample underwent a two-step amplification: the first 5 cycles were performed using the hybridisation temperature that excluded the restriction enzyme tail of the primer ($T_{m1}$). This was followed by 30 cycles according to the hybridisation temperature calculated for the whole length oligos ($T_{m2}$). Elongation times, performed at 68° C. or 72° C., varied according to the length of the Orf to be amplified. In the case of Orf1 the elongation time, starting from 3 minutes, was increased by 15 seconds each cycle. The cycles were completed with a 10 minute extension step at 72° C.

The amplified DNA was either loaded directly on a 1% agarose gel. The DNA fragment corresponding to the band of correct size was purified from the gel using the Qiagen Gel Extraction Kit, following the manufacturer's protocol.

The purified DNA corresponding to the amplified fragment was digested with the appropriate restriction enzymes for cloning into pET-21b+ or pET22b+. Digested fragments were purified using the QIAquick PCR purification kit (following the manufacturer's instructions) and eluted with either $H_2O$ or 10 mM Tris, pH 8.5. Plasmid vectors were digested with the appropriate restriction enzymes, loaded onto a 1.0% agarose gel and the band corresponding to the digested vector purified using the Qiagen QIAquick Gel Extraction Kit.

The fragments corresponding to each gene, previously digested and purified, were ligated into pET21b+ or into pET22b+. A molar ratio of 3:1 fragment/vector was used with T4 DNA ligase in the ligation buffer supplied by the manufacturer.

Recombinant plasmid was transformed into competent *E. coli* DH5 or HB101 by incubating the ligase reaction solution and bacteria for 40 minutes on ice, then at 37° C. for 3 minutes. This was followed by the addition of 800 µl LB broth and incubation at 37° C. for 20 minutes. The cells were centrifuged at maximum speed in an Eppendorf microfuge, resuspended in approximately 200 µl of the supernatant and plated onto LB ampicillin (100 mg/ml) agar.

Screening for recombinant clones was performed by growing randomly selected colonies overnight at 37° C. in 4.0 ml of LB broth+100 µg/ml ampicillin. Cells were pelleted and plasmid DNA extracted using the Qiagen QIAprep Spin Miniprep Kit, following the manufacturer's instructions. Approximately 1 µg of each individual miniprep was digested with the appropriate restriction enzymes and the digest loaded onto a 1-1.5% agarose gel (depending on the expected insert size), in parallel with the molecular weight marker (1 kb DNA Ladder, GIBCO). Positive clones were selected on the basis of the size of insert.

After cloning each gene into the expression vector, recombinant plasmids were transformed into *E. coli* strains suitable for expression of the recombinant protein. 1 µl of each construct was used to transform *E. coli* BL21-DE3 as described above. Single recombinant colonies were inoculated into 2 ml LB+Amp (100 µg/ml), incubated at 37° C. overnight, then diluted 1:30 in 20 ml of LB+Amp (100 µg/ml) in 100 ml flasks, to give an $OD_{600}$ between 0.1 and 0.2. The flasks were incubated at 30° C. or at 37° C. in a gyratory water bath shaker until $OD_{600}$ indicated exponential growth suitable for induction of expression (0.4-0.8 OD). Protein expression was induced by addition of 1.0 mM IPTG. After 3 hours incubation at 30° C. or 37° C. the $OD_{600}$ was measured and expression examined. 1.0 ml of each sample was centrifuged in a microfuge, the pellet resuspended in PBS and analysed by SDS-PAGE and Coomassie Blue staining.

The GST fusion protein was expressed, but it was found to be insoluble (i.e. unpurifiable). The His-fusion was expressed as insoluble protein.

For each clone purified as a His-fusion, a single colony was streaked and grown overnight at 37° C. on a LB/Amp (100 µg/ml) agar plate. An isolated colony from this plate was inoculated into 20 ml of LB/Amp (100 µg/ml) liquid medium and grown overnight at 37° C. with shaking. The overnight culture was diluted 1:30 into 1.0 L LB/Amp (100 µg/ml) liquid medium and allowed to grow at the optimal temperature (30 or 37° C.) until the $OD_{550}$ reached 0.6-0.8. Expression of recombinant protein was induced by addition of IPTG (final concentration 1.0 mM) and the culture incubated for a further 3 hours. Bacteria were harvested by centrifugation at 8000 g for 15 min at 4° C. The bacterial pellet was resuspended in 7.5 ml of buffer B (8M urea, 10 mM Tris-HCl, 100 mM phosphate buffer, pH 8.8). Cells were disrupted by sonication on ice four times for 30 sec at 40 W using a Branson sonifier 450 and centrifuged at 13 000×g for 30 min at 4° C. Pellets were resuspended in 2.0 ml buffer C (6 M guanidine hydrochloride, 100 mM phosphate buffer, 10 mM Tris-HCl, pH 7.5 and treated with 10 passes of a Dounce homogenizer. The homogenate was centrifuged at 13000 g for 30 min and the supernatant retained. Supernatants were mixed with 150 µl $Ni^{2+}$-resin (previously equilibrated with buffer B) and incubated at room temperature with gentle agitation for 30 min. The resin was Chelating Sepharose Fast Flow (Pharmacia), prepared according to the manufacturer's protocol. The batch-wise preparation was centrifuged at 700×g for 5 min at 4° C. and the supernatant discarded. The resin was washed twice (batch-wise) with 10 ml buffer B for 10 min, resuspended in 1.0 ml buffer B and loaded onto a disposable column. The resin continued to be washed with buffer B at room temperature, until the $OD_{280}$ of the flow-through reached 0.02-0.01. The resin was further washed with buffer D (8M urea, 10 mM Tris-HCl, 100 mM phosphate buffer, pH 6.3) until $OD_{280}$ of the flow-through reached 0.02-0.01. The His-fusion protein was eluted by addition of 700 µl of elution buffer B (8 M urea, 10 mM Tris-HCl, 100 mM phosphate buffer, pH 4.5) and fractions collected until the $OD_{280}$ indicated all the recombinant protein was obtained. 20 µl aliquots of each elution fraction were analysed by SDS-PAGE. Protein concentrations were estimated using the Bradford assay.

To renature the protein, glycerol was added to the denatured fractions obtained above to give a final concentration of 10% v/v. The proteins were diluted to 200 µg/ml using dialysis buffer I (10% v/v glycerol, 0.5M arginine, 50 mM phosphate buffer, 5.0 mM reduced glutathione, 0.5 mM oxidised glutathione, 2.0 M urea, pH 8.8) and dialysed against the same buffer for 12-14 hours at 4° C. Further dialysis was performed with buffer II (10% v/v glycerol, 0.5M arginine, 50 mM phosphate buffer, 5.0 mM reduced glutathione, 0.5 mM oxidised glutathione, pH 8.8) for 12-14 hours at 4° C. Protein concentration was estimated using the formula:

Protein(mg/ml)=$(1.55 \times OD_{280})-(0.76 \times OD_{260})$

For immunological characterisation of ORF21, Balb/C mice were immunized with antigens on days 0, 21 and 35 and sera analyzed at day 49.

ORF21 gave a positive results on the following ELISA assay: acapsulated MenB M7 and the capsulated strains were plated on chocolate agar plates and incubated overnight at 37° C. with 5% $CO_2$. Bacterial colonies were collected from the agar plates using a sterile dracon swab and inoculated into Mueller-Hinton Broth (Difco) containing 0.25% glucose. Bacterial growth was monitored every 30 minutes by following $OD_{620}$. The bacteria were let to grow until the OD reached the value of 0.4-0.5. The culture was centrifuged for 10 minutes at 400 rpm. The supernatant was discarded and bacteria were washed twice with PBS, resuspended in PBS containing 0.025% formaldehyde, and incubated for 1 hour at 37° C. and then overnight at 4° C. with stirring. 100 µl bacterial cells were added to each well of a 96 well Greiner plate and incubated overnight at 4° C. The wells were then washed three times with PBT washing buffer (0.1% Tween-20 in PBS). 200 µl of saturation buffer (2.7% polyvinylpyrrolidone 10 in water) was added to each well and the plates incubated for 2 hours at 37° C. Wells were washed three times with PBT. 200 µl of diluted sera (Dilution buffer: 1% BSA, 0.1% Tween-20, 0.1% $NaN_3$ in PBS) were added to each well and the plates incubated for 2 hours at 37° C. Wells were washed three times with PBT. 100 µl of HRP-conjugated rabbit anti-mouse (Dako) serum diluted 1:2000 in dilution buffer were added to each well and the plates were incubated for 90 minutes at 37° C. Wells were washed three times with PBT buffer. 100 µl of substrate buffer for HRP (25 ml of citrate buffer pH5, 10 mg of O-phenildiamine and 10 µl of $H_2O_2$) were added to each well and the plates were left at room temperature for 20 minutes. 100 µl 12.5% $H_2SO_4$ was added to each well and $OD_{490}$ was followed. The ELISA titers were calculated abitrarely as the dilution of sera which gave an $OD_{490}$ value of 0.4 above the level of preimmune sera. The ELISA was considered positive when the dilution of sera with $OD_{490}$ of 0.4 was higher than 1:400.

To assess cellular location of ORF21, the following FACS assay was used: acapsulated MenB M7 strain was plated on chocolate agar plates and incubated overnight at 37° C. with 5% $CO_2$. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following $OD_{620}$. The bacteria were let to grow until the OD reached the value of 0.35-0.5. The culture was centrifuged for 10 minutes at 4000 rpm. The supernatant was discarded and the pellet was resuspended in blocking buffer (1% BSA in PBS, 0.4% $NaN_3$) and centrifuged for 5 minutes at 400 rpm. Cells were resuspended in blocking buffer to reach $OD_{620}$ of 0.05. 100 µl bacterial cells were added to each well of a Costar 96 well plate. 100 µl of diluted (1:100, 1:200, 1:400) sera (in blocking buffer) were added to each well and plates incubated for 2 hours at 4° C. Cells were centrifuged for 5 minutes at 4000 rpm, the supernatant aspirated and cells washed by addition of 200 µl/well of blocking buffer in each well. 100 µl of R-Phicoerytrin conjugated $F(ab)_2$ goat anti-mouse, diluted 1:100, was added to each well and plates incubated for 1 hour at 4° C. Cells were spun down by centrifugation at 4000 rpm for 5 minutes and washed by addition of 200 µl/well of blocking buffer. The supernatant was aspirated and cells resuspended in 200 µl/well of PBS, 0.25% formaldehyde. Samples were transferred to FACScan tubes and read. The condition for FACScan (Laser Power 15 mW) setting were: FL2 on; FSC-H threshold: 92; FSC PMT Voltage: E 01; SSC PMT: 474; Amp. Gains 6.1; FL-2 PMT: 586; compensation values: 0.

As well as FACS, Western analysis was used to assess cellular location: purified proteins (500 ng/lane), outer membrane vesicles (5 µg) and total cell extracts (25 µg) derived from MenB strain 2996 were loaded onto a 12% SDS-polyacrylamide gel and transferred to a nitrocellulose membrane. The transfer was performed for 2 hours at 150 mA at 4° C., using transfer buffer (0.3% Tris base, 1.44% glycine, 20% (v/v) methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4CN Substrate Kit (Bio-Rad). The reaction was stopped by adding water.

The OMVs were prepared as follows: *N. meningitidis* strain 2996 was grown overnight at 37 degrees with 5% $CO_2$ on 5 GC plates, harvested with a loop and resuspended in 10 ml of 20 mM Tris-HCl pH 7.5, 2 mM EDTA. Heat inactivation was performed at 56° C. for 45 minutes and the bacteria disrupted by sonication for 5 minutes on ice (50% duty cycle, 50% output, Branson sonifier 3 mm microtip). Unbroken cells were removed by centrifugation at 5000 g for 10 minutes, the supernatant containing the total cell envelope fraction recovered and further centrifuged overnight at 50000 g at the temperature of 4° C. The pellet containing the membranes was resuspended in 2% sarkosyl, 20 mM Tris-HCl pH 7.5, 2 mM EDTA and incubated at room temperature for 20 minutes to solubilyze the inner membranes. The suspension was centrifuged at 10000 g for 10 minutes to remove aggregates, the supernatant was further centrifuged at 50000 g for 3 hours. The pellet, containing the outer membranes was washed in PBS and resuspended in the same buffer. The protein concentration was measured by the D.C. Bio-Rad Protein assay (Modified Lowry method), using BSA as a standard.

Total cell extracts were prepared as follows: N. meningitidis strain 2996 was grown overnight on a GC plate, harvested with a loop and resuspended in 1 ml of 20 mM Tris-HCl. Heat inactivation was performed at 56° C. for 30 minutes.

ELISA, FACS and Western analysis all show that ORF21 is surface-exposed.

ORF21 gave good results using the following bactericidal assay: N. meningitidis strain 2996 was grown overnight at 37° C. on chocolate agar plates (starting from a frozen stock) with 5% $CO_2$. Colonies were collected and used to inoculate 7 ml Mueller-Hinton broth, containing 0.25% glucose to reach an $OD_{620}$ of 0.05-0.08. The culture was incubated for approximately 1.5 hours at 37 degrees with shacking until the $OD_{620}$ reached the value of 0.23-0.24. Bacteria were diluted in 50 mM Phosphate buffer pH 7.2 containing 1 mM $MgCl_2$, 10 mM $CaCl_2$ and 0.5% (w/v) BSA (assay buffer) at the working dilution of $10^5$ CFU/ml. The total volume of the final reaction mixture was 50 µl with 25 µl of serial two fold dilution of test serum, 12.5 µl of bacteria at the working dilution, 12.5 µl of baby rabbit complement (final concentration 25%). Controls included bacteria incubated with complement serum, immune sera incubated with bacteria and with complement inactivated by heating at 56° C. for 30'. Immediately after the addition of the baby rabbit complement, 10 µl of the controls were plated on Mueller-Hinton agar plates using the tilt method (time 0). The 96-wells plate was incubated for 1 hour at 37° C. with rotation. 7 µl of each sample were plated on Mueller-Hinton agar plates as spots, whereas 10 µl of the controls were plated using the tilt method (time 1). Agar plates were incubated for 18 hours at 37 degrees and the colonies corresponding to time 0 and time 1 were counted.

Computer Analysis

FIG. 1 shows the sequence of ORF21, together with computer analysis data.

ORF21 has the following AMPHI regions [Gao et al. (1989) J. Immunol. 143:3007; Roberts et al. (1996) AIDS Res Hum Retrovir 12:593; Quakyi et al. (1992) Scand J Immunol suppl. 11:9]: SEQ IDs 14 to 32.

The antigenic index algorithm identified the following regions: SEQ IDs 33 to 70.

Hopp & Woods analysis reveals the following hydrophilic regions: SEQ IDs 71 to 104.

SEQ IDs 14-104 may be used as these oligopeptides, or as part of longer polypeptides.

An alignment of ORF21 sequences from MenA, MenB and gonococcus is shown in FIG. 2.

Vaccines

The three proteins identified above are expressed and used for immunisation. Good immune responses are observed against the proteins.

Combination Vaccines

In addition, the proteins are each combined with antigens against other pathogenic organisms (e.g. the Chiron polysaccharide vaccine against serogroup C meningitis). and used for immunisation. Good immune responses are observed.

It will be understood that the invention has been described by way of example only and modifications may be made whilst remaining within the scope and spirit of the invention.

What is claimed is:

1. An isolated oligopeptide consisting of the amino acid sequence comprising SEQ ID NO:89.

2. A composition comprising the oligopeptide of claim 1, and a pharmaceutically acceptable vehicle.

3. The composition of claim 2, further comprising one or more immunogenic components selected from the group consisting of (a) a protective antigen against *Neisseria meningitidis* serogroup B; (b) a protective antigen against *Neisseria gonorrhoeae*; (c) a protective antigen against *Neisseria meningitidis* serogroup A; (d) a protective antigen against *Neisseria meningitidis* serogroup C; (e) a protective antigen against *Neisseria meningitidis* serogroup Y; (f) a protective antigen against *Neisseria meningitidis* serogroup W; (g) a protective antigen against *Haemophilus influenzae*; (h) a protective antigen against pneumococcus; (i) a protective antigen against diphtheria; (j) a protective antigen against tetanus; (k) a protective antigen against whooping cough; (l) a protective antigen against *Helicobacter pylori*; (m) a protective antigen against polio; and (n) a protective antigen against hepatitis B virus.

* * * * *

SEQUENCE LISTING

```
<160> NUMBER OF SEQ ID NOS: 106

<210> SEQ ID NO 1
<211> LENGTH: 15
<212> TYPE: PRT
<213> ORGANISM: Neisseria meningitidis

<400> SEQUENCE: 1

Asp Phe Thr Ile Gln Asp Ile Arg Val Glu Gly Leu Gln Arg Thr
1               5                   10                  15

<210> SEQ ID NO 2
<211> LENGTH: 2394
<212> TYPE: DNA
<213> ORGANISM: Neisseria meningitidis

<400> SEQUENCE: 2
atgaaactga aacagattgc ttccgcactg atgatgttgg gcatatcgcc tttggcactt      60
gccgacttca ccatccaaga catccgcgtc gaaggcttgc agcgtaccga gccgagtacc     120
gtattcaact acctgcccgt caaagtcggc gacacctaca acgacacaca cggcagtgcc     180
atcatcaaaa gcctgtacgc caccggtttc tttgacgacg tacgcgtcga aactgcggac     240
gggcagctcc tgctgaccgt tatcgaacgc cccaccatcg gctcgctcaa catcaccggc     300
```

-continued

```
gcaaaaatgc tgcaaaacga cgccattaag aaaaacctcg aatcgttcgg gctggcgcag        360
tcgcaatact ttaatcaggc gacactcaat caggcagtcg ccggcctgaa agaagaatac        420
ctcgggcgcg gcaaactcaa tatccaaatc acgcccaaag taaccaaact cgcccgcaac        480
cgcgtcgaca tcgacatcac gattgacgag ggcaaatccg ccaaaatcac cgacatcgaa        540
tttgaaggca accaagtcta ttccgaccgc aaactgatgc ggcaaatgtc cctgaccgaa        600
ggcggcattt ggacatggct gacacgaagc aaccaattca cgagcagaa atttgcccaa         660 gatatggaaa aagtaaccga cttctaccaa ataacggct acttcgattt ccgtatcctc         720
gataccgaca tccaaaccaa cgaagacaaa accaagcaga ccatcaaaat caccgtccac        780
gaaggcggac gtttccgttg ggcaaagtc tccatcgaag cgacaccaa cgaagtcccc         840 aaagccgaac tggaaaaact gctgaccatg aagcccggca atggtacga acgccagcag        900 atgaccgccg ttttgggtga gattcagaac cgcatgggct cggcaggcta cgcatacagc        960
gaaatcagcg tacagccgct gccgaacgct gaaaccaaaa ccgtcgattt cgtcctgcac       1020
atcgaaccgg gccggaaaat ctacgtcaac gaaatacaca tcaccggcaa caacaaaacc       1080
cgcgacgaag tcgtccgccg tgaattacgc caaatggaat ccgcaccta cgacacctcc        1140 aagctgcaac gttccaaaga gcgcgtcgag ctttttgggct acttcgacaa tgtccagttt       1200
gatgctgtcc cgcttgccgg cacgcccgac aaagtcgatt tgaacatgag tctgaccgaa       1260
cgttccaccg gttccctgga tttgagcgcg ggttgggttc aagataccgg gttggtcatg       1320
tccgcaggcg tttcccaaga caacctgttc ggtacgggca agtcggccgc actgcgcgcc       1380
tccaggagca aaaccacgct taacggctcg ctgtcgtttta ctgacccgta cttcacggca       1440
gacggggtca gcctgggcta cgatgtttac ggaaaagcct tcgacccgcg caaagcatcg       1500
accagcatca acaatataa aaccaccacg gcaggcgcag gcatccgcat gagcgtgcct        1560
gttaccgaat acgaccgcgt gaatttcggt ttggtggcag aacacctgac cgtcaacacc        1620
tacaacaaag cgcccaaaca ctatgccgac tttatcaaga aatacggcaa accgacggc        1680 acagacggca gcttcaaagg ctggctgtac aaaggtaccg tcggctgggg cgcaacaaa         1740 accgacagcg cgttatggcc gacgcgcggc tacctgacgg gcgtgaacgc cgaaatcgcc       1800
ctgcctggca gcaaactgca atactactcc gccacccaca accaaacctg gttcttcccc       1860
ctgagcaaaa ccttcacgct gatgctcggc ggcgaagtcg gcattgcggg cggctacggc       1920
agaaccaaag aaatcccctt ctttgaaaac ttctacggcg gcggcctggg ttcggtgcgc       1980
ggatacgaaa gcggcacgct cggtccgaaa gtctatgacg aatacggcga aaaatcagc        2040 tacgcggca caaaaaagc caacgtctcc gccgagctgc tcttcccgat gcccggcgcg        2100
aaagacgcgc gcaccgtccg cctgagcctg tttgccgacg caggcagcgt gtgggacggc       2160
aaaacctacg acgacaacag cagttccgcg accggcggca gggttcaaaa catttacggc       2220
gccggcaata cccataaatc cacctttacc aacgaattgc gctattccgc cggcggcgcg       2280
gttacctggc tctcgccttt aggcccgatg aaattcagct acgcctaccc gctgaagaaa       2340
aaaccggaag acgaaatcca acgcttccaa ttccaactcg gcacgacgtt ctaa              2394
```

<210> SEQ ID NO 3
<211> LENGTH: 797
<212> TYPE: PRT
<213> ORGANISM: Neisseria meningitidis

<400> SEQUENCE: 3

-continued

```
Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
            85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
```

```
                420             425             430
Val Gln Asp Thr Gly Leu Val Met Ser Ala Gly Val Ser Gln Asp Asn
            435             440             445
Leu Phe Gly Thr Gly Lys Ser Ala Ala Leu Arg Ala Ser Arg Ser Lys
        450             455             460
Thr Thr Leu Asn Gly Ser Leu Ser Phe Thr Asp Pro Tyr Phe Thr Ala
465             470             475             480
Asp Gly Val Ser Leu Gly Tyr Asp Val Tyr Gly Lys Ala Phe Asp Pro
                485             490             495
Arg Lys Ala Ser Thr Ser Ile Lys Gln Tyr Lys Thr Thr Thr Ala Gly
            500             505             510
Ala Gly Ile Arg Met Ser Val Pro Val Thr Glu Tyr Asp Arg Val Asn
            515             520             525
Phe Gly Leu Val Ala Glu His Leu Thr Val Asn Thr Tyr Asn Lys Ala
        530             535             540
Pro Lys His Tyr Ala Asp Phe Ile Lys Lys Tyr Gly Lys Thr Asp Gly
545             550             555             560
Thr Asp Gly Ser Phe Lys Gly Trp Leu Tyr Lys Gly Thr Val Gly Trp
                565             570             575
Gly Arg Asn Lys Thr Asp Ser Ala Leu Trp Pro Thr Arg Gly Tyr Leu
            580             585             590
Thr Gly Val Asn Ala Glu Ile Ala Leu Pro Gly Ser Lys Leu Gln Tyr
        595             600             605
Tyr Ser Ala Thr His Asn Gln Thr Trp Phe Pro Leu Ser Lys Thr
        610             615             620
Phe Thr Leu Met Leu Gly Gly Glu Val Gly Ile Ala Gly Gly Tyr Gly
625             630             635             640
Arg Thr Lys Glu Ile Pro Phe Phe Glu Asn Phe Tyr Gly Gly Leu
            645             650             655
Gly Ser Val Arg Gly Tyr Glu Ser Gly Thr Leu Gly Pro Lys Val Tyr
            660             665             670
Asp Glu Tyr Gly Glu Lys Ile Ser Tyr Gly Asn Lys Lys Ala Asn
            675             680             685
Val Ser Ala Glu Leu Leu Phe Pro Met Pro Gly Ala Lys Asp Ala Arg
        690             695             700
Thr Val Arg Leu Ser Leu Phe Ala Asp Ala Gly Ser Val Trp Asp Gly
705             710             715             720
Lys Thr Tyr Asp Asp Asn Ser Ser Ala Thr Gly Gly Arg Val Gln
                725             730             735
Asn Ile Tyr Gly Ala Gly Asn Thr His Lys Ser Thr Phe Thr Asn Glu
            740             745             750
Leu Arg Tyr Ser Ala Gly Gly Ala Val Thr Trp Leu Ser Pro Leu Gly
        755             760             765
Pro Met Lys Phe Ser Tyr Ala Tyr Pro Leu Lys Lys Lys Pro Glu Asp
        770             775             780
Glu Ile Gln Arg Phe Gln Phe Gln Leu Gly Thr Thr Phe
785             790             795

<210> SEQ ID NO 4
<211> LENGTH: 21
<212> TYPE: PRT
<213> ORGANISM: Neisseria meningitidis

<400> SEQUENCE: 4
```

```
Met Lys Leu Lys Gln Ile Ala Ser Ala Leu Met Met Leu Gly Ile Ser
1               5                   10                  15

Pro Leu Ala Leu Ala
            20
```

<210> SEQ ID NO 5
<211> LENGTH: 776
<212> TYPE: PRT
<213> ORGANISM: Neisseria meningitidis

<400> SEQUENCE: 5

```
Asp Phe Thr Ile Gln Asp Ile Arg Val Glu Gly Leu Gln Arg Thr Glu
1               5                   10                  15

Pro Ser Thr Val Phe Asn Tyr Leu Pro Val Lys Val Gly Asp Thr Tyr
                20                  25                  30

Asn Asp Thr His Gly Ser Ala Ile Ile Lys Ser Leu Tyr Ala Thr Gly
            35                  40                  45

Phe Phe Asp Asp Val Arg Val Glu Thr Ala Asp Gly Gln Leu Leu Leu
    50                  55                  60

Thr Val Ile Glu Arg Pro Thr Ile Gly Ser Leu Asn Ile Thr Gly Ala
65                  70                  75                  80

Lys Met Leu Gln Asn Asp Ala Ile Lys Lys Asn Leu Glu Ser Phe Gly
                85                  90                  95

Leu Ala Gln Ser Gln Tyr Phe Asn Gln Ala Thr Leu Asn Gln Ala Val
            100                 105                 110

Ala Gly Leu Lys Glu Glu Tyr Leu Gly Arg Gly Lys Leu Asn Ile Gln
        115                 120                 125

Ile Thr Pro Lys Val Thr Lys Leu Ala Arg Asn Arg Val Asp Ile Asp
130                 135                 140

Ile Thr Ile Asp Glu Gly Lys Ser Ala Lys Ile Thr Asp Ile Glu Phe
145                 150                 155                 160

Glu Gly Asn Gln Val Tyr Ser Asp Arg Lys Leu Met Arg Gln Met Ser
                165                 170                 175

Leu Thr Glu Gly Gly Ile Trp Thr Trp Leu Thr Arg Ser Asn Gln Phe
            180                 185                 190

Asn Glu Gln Lys Phe Ala Gln Asp Met Glu Lys Val Thr Asp Phe Tyr
        195                 200                 205

Gln Asn Asn Gly Tyr Phe Asp Phe Arg Ile Leu Asp Thr Asp Ile Gln
    210                 215                 220

Thr Asn Glu Asp Lys Thr Lys Gln Thr Ile Lys Ile Thr Val His Glu
225                 230                 235                 240

Gly Gly Arg Phe Arg Trp Gly Lys Val Ser Ile Glu Gly Asp Thr Asn
                245                 250                 255

Glu Val Pro Lys Ala Glu Leu Glu Lys Leu Leu Thr Met Lys Pro Gly
            260                 265                 270

Lys Trp Tyr Glu Arg Gln Gln Met Thr Ala Val Leu Gly Glu Ile Gln
        275                 280                 285

Asn Arg Met Gly Ser Ala Gly Tyr Ala Tyr Ser Glu Ile Ser Val Gln
    290                 295                 300

Pro Leu Pro Asn Ala Glu Thr Lys Thr Val Asp Phe Val Leu His Ile
305                 310                 315                 320

Glu Pro Gly Arg Lys Ile Tyr Val Asn Glu Ile His Ile Thr Gly Asn
                325                 330                 335

Asn Lys Thr Arg Asp Glu Val Val Arg Arg Glu Leu Arg Gln Met Glu
            340                 345                 350
```

```
Ser Ala Pro Tyr Asp Thr Ser Lys Leu Gln Arg Ser Lys Glu Arg Val
        355                 360                 365

Glu Leu Leu Gly Tyr Phe Asp Asn Val Gln Phe Asp Ala Val Pro Leu
        370                 375                 380

Ala Gly Thr Pro Asp Lys Val Asp Leu Asn Met Ser Leu Thr Glu Arg
385                 390                 395                 400

Ser Thr Gly Ser Leu Asp Leu Ser Ala Gly Trp Val Gln Asp Thr Gly
                405                 410                 415

Leu Val Met Ser Ala Gly Val Ser Gln Asp Asn Leu Phe Gly Thr Gly
            420                 425                 430

Lys Ser Ala Ala Leu Arg Ala Ser Arg Ser Lys Thr Thr Leu Asn Gly
        435                 440                 445

Ser Leu Ser Phe Thr Asp Pro Tyr Phe Thr Ala Asp Gly Val Ser Leu
        450                 455                 460

Gly Tyr Asp Val Tyr Gly Lys Ala Phe Asp Pro Arg Lys Ala Ser Thr
465                 470                 475                 480

Ser Ile Lys Gln Tyr Lys Thr Thr Ala Gly Ala Gly Ile Arg Met
                485                 490                 495

Ser Val Pro Val Thr Glu Tyr Asp Arg Val Asn Phe Gly Leu Val Ala
            500                 505                 510

Glu His Leu Thr Val Asn Thr Tyr Asn Lys Ala Pro Lys His Tyr Ala
        515                 520                 525

Asp Phe Ile Lys Lys Tyr Gly Lys Thr Asp Gly Thr Asp Gly Ser Phe
        530                 535                 540

Lys Gly Trp Leu Tyr Lys Gly Thr Val Gly Trp Gly Arg Asn Lys Thr
545                 550                 555                 560

Asp Ser Ala Leu Trp Pro Thr Arg Gly Tyr Leu Thr Gly Val Asn Ala
                565                 570                 575

Glu Ile Ala Leu Pro Gly Ser Lys Leu Gln Tyr Tyr Ser Ala Thr His
            580                 585                 590

Asn Gln Thr Trp Phe Phe Pro Leu Ser Lys Thr Phe Thr Leu Met Leu
        595                 600                 605

Gly Gly Glu Val Gly Ile Ala Gly Gly Tyr Gly Arg Thr Lys Glu Ile
        610                 615                 620

Pro Phe Phe Glu Asn Phe Tyr Gly Gly Leu Gly Ser Val Arg Gly
625                 630                 635                 640

Tyr Glu Ser Gly Thr Leu Gly Pro Lys Val Tyr Asp Glu Tyr Gly Glu
                645                 650                 655

Lys Ile Ser Tyr Gly Gly Asn Lys Lys Ala Asn Val Ser Ala Glu Leu
            660                 665                 670

Leu Phe Pro Met Pro Gly Ala Lys Asp Ala Arg Thr Val Arg Leu Ser
        675                 680                 685

Leu Phe Ala Asp Ala Gly Ser Val Trp Asp Gly Lys Thr Tyr Asp Asp
        690                 695                 700

Asn Ser Ser Ser Ala Thr Gly Gly Arg Val Gln Asn Ile Tyr Gly Ala
705                 710                 715                 720

Gly Asn Thr His Lys Ser Thr Phe Thr Asn Glu Leu Arg Tyr Ser Ala
                725                 730                 735

Gly Gly Ala Val Thr Trp Leu Ser Pro Leu Gly Pro Met Lys Phe Ser
            740                 745                 750

Tyr Ala Tyr Pro Leu Lys Lys Lys Pro Glu Asp Glu Ile Gln Arg Phe
        755                 760                 765
```

```
Gln Phe Gln Leu Gly Thr Thr Phe
    770                 775

<210> SEQ ID NO 6
<211> LENGTH: 2379
<212> TYPE: DNA
<213> ORGANISM: Neisseria meningitidis

<400> SEQUENCE: 6
atgaaactga aacagattgc ctccgcactg atgatgttgg gcatatcgcc tttggcattt      60
gccgacttca ccatccaaga catccgtgtc gaaggcttgc agcgtaccga gccgagcacc     120
gtattcaact acctgcccgt caaagtcggc gacacctaca cgacacaca  cggcagtgcc     180
atcatcaaaa gcctgtacgc caccggtttc tttgacgacg tacgagtcga aactgcggac     240
gggcagcttc tgctgaccgt tatcgaacgc cccaccatcg gctcgctcaa catcaccggc     300
gccaaaatgc tgcaaaacga cgccatcaag aaaaaacctcg aatcgttcgg gctggcgcag     360
tcgcaatact ttaatcaggc gacactcaac caggcagtcg ccggcctgaa agaagaatac     420
ctcgggcgtg gcaaactcaa tatccaaatc acgcccaaag taaccaaact cgcccgcaac     480
cgcgtcgaca tcgacatcac gattgacgag ggcaaatccg ccaaaatcac cgacatcgaa     540
tttgaaggca accaagtcta ttccgaccgc aaactgatgc ggcagatgtc gctgaccgaa     600
ggcggcattt ggacatggct gacacgaagc gaccggttcg accgcagaa  attcgcccaa     660
gacatggaaa agtaaccga  cttctaccag aacaacggct acttcgattt ccgtatcctc     720
gataccgaca tccaaaccaa cgaagacaaa accaggcaga ccatcaaaat caccgtccac     780
gaaggcggac gtttccgctg gggcaaagtg tcgattgaag cgacaccaa  cgaagtcccc     840
aaggccgaac tggaaaaact gctgaccatg aagcccggca atggtacga  acgccagcag     900
atgaccgccg ttttgggtga gattcagaac cgcatgggct cggcaggcta cgcatacagc     960
gaaatcagcg tacagccgct gccgaacgcc ggaaccaaaa ccgtcgattt cgtcctgcac    1020
atcgaaccgg gccggaaaat ctacgtcaac gaaatccaca tcaccggcaa caacaaaacc    1080
cgcgacgaag tcgtgcgccg cgaattgcgc caaatggaat ccgcgcctta cgacacctcc    1140
aagctgcaac gctccaaaga gcgcgtcgag cttttgggct acttcgacaa cgtacagttt    1200
gatgccgtcc cgcttgccgg tacgcccgac aaagtcgatt tgaacatgag cctgaccgaa    1260
cgctccaccg gctcgctcga cttgagcgcg ggctgggttc aggataccgg cttggtcatg    1320
tccgccggcg tatcgcagga caacctgttc ggtacgggca gtcggccgc  cctgcgcgcc    1380
tcgcgaagca aaaccacgct caacggctcg ctgtcgttta ccgacccgta cttcacggca    1440
gacggggtca gcctgggcta cgatatttac ggaaaagcct tcgacccgcg caaagcatcg    1500
accagcgtca acaatataa  aaccaccacc gccggcggcg gcgtaaggat gggtatcccc    1560
gttaccgaat cgaccgcgt  caatttcggg ctggcggcgg aacacctgac cgtcaacacc    1620
tacaacaaag cacccaaacg ctatgccgac tttatcagga aatacggcaa aaccgacggc    1680
gcagacggca gcttcaaagg cctgctgtac aaaggcaccg tcggctgggg cgcaacaag    1740
accgacagcg cgtcatggcc gacgcgcggc tacctgaccg gcgtaaatgc cgaaatcgcc    1800
ctgcccggca gcaaactgca atactactcc gccacccaca accaaacctg gttcttcccc    1860
ttaagcaaaa ccttcacgct gatgctcggc ggcgaagtcg gcattgcggg cggctacggc    1920
agaaccaaag aaatccccct ctttgaaaac ttctacggcg cgggcctggg ttcggtgcgc    1980
ggctacgaaa gcggcacgct cggcccgaaa gtgtatgacg aatacggcga aaaaatcagc    2040
```

```
tacggcggca acaaaaaagc caacgtctcc gccgagctgc tcttcccgat gcccggtgcg    2100
aaagacgcac gcaccgtccg cctgagcctg tttgccgacg caggcagcgt gtgggacggc    2160
agaacctata ccgccgccga aaacggtaac aacaaatcgg tttactcgga aaacgcgcat    2220
aaatccacct ttaccaacga attgcgctat tccgccggcg gcgcggttac ctggctctcg    2280
cctttgggtc cgatgaaatt cagctacgcc taccgctga agaaaaaacc ggaagacgaa    2340
atccaacgct tccaattcca gctcggcacg acgttctaa                          2379
```

<210> SEQ ID NO 7
<211> LENGTH: 792
<212> TYPE: PRT
<213> ORGANISM: Neisseria meningitidis

<400> SEQUENCE: 7

```
Met Lys Leu Lys Gln Ile Ala Ser Ala Leu Met Met Leu Gly Ile Ser
1               5                   10                  15

Pro Leu Ala Phe Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asp Arg Phe Asp Arg Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Arg Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320
```

-continued

```
Glu Ile Ser Val Gln Pro Leu Pro Asn Ala Gly Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
            420                 425                 430

Val Gln Asp Thr Gly Leu Val Met Ser Ala Gly Val Ser Gln Asp Asn
        435                 440                 445

Leu Phe Gly Thr Gly Lys Ser Ala Ala Leu Arg Ala Ser Arg Ser Lys
    450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Ile Tyr Gly Lys Ala Phe Asp Pro
                485                 490                 495

Arg Lys Ala Ser Thr Ser Val Lys Gln Tyr Lys Thr Thr Ala Gly
            500                 505                 510

Gly Gly Val Arg Met Gly Ile Pro Val Thr Glu Tyr Asp Arg Val Asn
        515                 520                 525

Phe Gly Leu Ala Ala Glu His Leu Thr Val Asn Thr Tyr Asn Lys Ala
    530                 535                 540

Pro Lys Arg Tyr Ala Asp Phe Ile Arg Lys Tyr Gly Lys Thr Asp Gly
545                 550                 555                 560

Ala Asp Gly Ser Phe Lys Gly Leu Leu Tyr Lys Gly Thr Val Gly Trp
                565                 570                 575

Gly Arg Asn Lys Thr Asp Ser Ala Ser Trp Pro Thr Arg Gly Tyr Leu
            580                 585                 590

Thr Gly Val Asn Ala Glu Ile Ala Leu Pro Gly Ser Lys Leu Gln Tyr
        595                 600                 605

Tyr Ser Ala Thr His Asn Gln Thr Trp Phe Pro Leu Ser Lys Thr
    610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
        675                 680                 685

Val Ser Ala Glu Leu Leu Phe Pro Met Pro Gly Ala Lys Asp Ala Arg
    690                 695                 700

Thr Val Arg Leu Ser Leu Phe Ala Asp Ala Gly Ser Val Trp Asp Gly
705                 710                 715                 720

Arg Thr Tyr Thr Ala Ala Glu Asn Gly Asn Asn Lys Ser Val Tyr Ser
                725                 730                 735
```

Glu Asn Ala His Lys Ser Thr Phe Thr Asn Glu Leu Arg Tyr Ser Ala
            740                 745                 750

Gly Gly Ala Val Thr Trp Leu Ser Pro Leu Gly Pro Met Lys Phe Ser
            755                 760                 765

Tyr Ala Tyr Pro Leu Lys Lys Lys Pro Glu Asp Glu Ile Gln Arg Phe
            770                 775                 780

Gln Phe Gln Leu Gly Thr Thr Phe
785                 790

<210> SEQ ID NO 8
<211> LENGTH: 21
<212> TYPE: PRT
<213> ORGANISM: Neisseria meningitidis

<400> SEQUENCE: 8

Met Lys Leu Lys Gln Ile Ala Ser Ala Leu Met Met Leu Gly Ile Ser
1               5                   10                  15

Pro Leu Ala Phe Ala
            20

<210> SEQ ID NO 9
<211> LENGTH: 771
<212> TYPE: PRT
<213> ORGANISM: Neisseria meningitidis

<400> SEQUENCE: 9

Asp Phe Thr Ile Gln Asp Ile Arg Val Glu Gly Leu Gln Arg Thr Glu
1               5                   10                  15

Pro Ser Thr Val Phe Asn Tyr Leu Pro Val Lys Val Gly Asp Thr Tyr
            20                  25                  30

Asn Asp Thr His Gly Ser Ala Ile Ile Lys Ser Leu Tyr Ala Thr Gly
            35                  40                  45

Phe Phe Asp Asp Val Arg Val Glu Thr Ala Asp Gly Gln Leu Leu Leu
        50                  55                  60

Thr Val Ile Glu Arg Pro Thr Ile Gly Ser Leu Asn Ile Thr Gly Ala
65                  70                  75                  80

Lys Met Leu Gln Asn Asp Ala Ile Lys Lys Asn Leu Glu Ser Phe Gly
            85                  90                  95

Leu Ala Gln Ser Gln Tyr Phe Asn Gln Ala Thr Leu Asn Gln Ala Val
            100                 105                 110

Ala Gly Leu Lys Glu Glu Tyr Leu Gly Arg Gly Lys Leu Asn Ile Gln
            115                 120                 125

Ile Thr Pro Lys Val Thr Lys Leu Ala Arg Asn Arg Val Asp Ile Asp
            130                 135                 140

Ile Thr Ile Asp Glu Gly Lys Ser Ala Lys Ile Thr Asp Ile Glu Phe
145                 150                 155                 160

Glu Gly Asn Gln Val Tyr Ser Asp Arg Lys Leu Met Arg Gln Met Ser
            165                 170                 175

Leu Thr Glu Gly Gly Ile Trp Thr Trp Leu Thr Arg Ser Asp Arg Phe
            180                 185                 190

Asp Arg Gln Lys Phe Ala Gln Asp Met Glu Lys Val Thr Asp Phe Tyr
            195                 200                 205

Gln Asn Asn Gly Tyr Phe Asp Phe Arg Ile Leu Asp Thr Asp Ile Gln
            210                 215                 220

Thr Asn Glu Asp Lys Thr Arg Gln Thr Ile Lys Ile Thr Val His Glu
225                 230                 235                 240

-continued

```
Gly Gly Arg Phe Arg Trp Gly Lys Val Ser Ile Glu Gly Asp Thr Asn
                245                 250                 255

Glu Val Pro Lys Ala Glu Leu Glu Lys Leu Leu Thr Met Lys Pro Gly
            260                 265                 270

Lys Trp Tyr Glu Arg Gln Gln Met Thr Ala Val Leu Gly Glu Ile Gln
        275                 280                 285

Asn Arg Met Gly Ser Ala Gly Tyr Ala Tyr Ser Glu Ile Ser Val Gln
    290                 295                 300

Pro Leu Pro Asn Ala Gly Thr Lys Thr Val Asp Phe Val Leu His Ile
305                 310                 315                 320

Glu Pro Gly Arg Lys Ile Tyr Val Asn Glu Ile His Ile Thr Gly Asn
                325                 330                 335

Asn Lys Thr Arg Asp Glu Val Val Arg Arg Glu Leu Arg Gln Met Glu
            340                 345                 350

Ser Ala Pro Tyr Asp Thr Ser Lys Leu Gln Arg Ser Lys Glu Arg Val
        355                 360                 365

Glu Leu Leu Gly Tyr Phe Asp Asn Val Gln Phe Asp Ala Val Pro Leu
    370                 375                 380

Ala Gly Thr Pro Asp Lys Val Asp Leu Asn Met Ser Leu Thr Glu Arg
385                 390                 395                 400

Ser Thr Gly Ser Leu Asp Leu Ser Ala Gly Trp Val Gln Asp Thr Gly
                405                 410                 415

Leu Val Met Ser Ala Gly Val Ser Gln Asp Asn Leu Phe Gly Thr Gly
            420                 425                 430

Lys Ser Ala Ala Leu Arg Ala Ser Arg Ser Lys Thr Thr Leu Asn Gly
        435                 440                 445

Ser Leu Ser Phe Thr Asp Pro Tyr Phe Thr Ala Asp Gly Val Ser Leu
    450                 455                 460

Gly Tyr Asp Ile Tyr Gly Lys Ala Phe Asp Pro Arg Lys Ala Ser Thr
465                 470                 475                 480

Ser Val Lys Gln Tyr Lys Thr Thr Ala Gly Gly Val Arg Met
                485                 490                 495

Gly Ile Pro Val Thr Glu Tyr Asp Arg Val Asn Phe Gly Leu Ala Ala
            500                 505                 510

Glu His Leu Thr Val Asn Thr Tyr Asn Lys Ala Pro Lys Arg Tyr Ala
        515                 520                 525

Asp Phe Ile Arg Lys Tyr Gly Lys Thr Asp Gly Ala Asp Gly Ser Phe
    530                 535                 540

Lys Gly Leu Leu Tyr Lys Gly Thr Val Gly Trp Gly Arg Asn Lys Thr
545                 550                 555                 560

Asp Ser Ala Ser Trp Pro Thr Arg Gly Tyr Leu Thr Gly Val Asn Ala
                565                 570                 575

Glu Ile Ala Leu Pro Gly Ser Lys Leu Gln Tyr Tyr Ser Ala Thr His
            580                 585                 590

Asn Gln Thr Trp Phe Phe Pro Leu Ser Lys Thr Phe Thr Leu Met Leu
        595                 600                 605

Gly Gly Glu Val Gly Ile Ala Gly Gly Tyr Gly Arg Thr Lys Glu Ile
    610                 615                 620

Pro Phe Phe Glu Asn Phe Tyr Gly Gly Leu Gly Ser Val Arg Gly
625                 630                 635                 640

Tyr Glu Ser Gly Thr Leu Gly Pro Lys Val Tyr Asp Glu Tyr Gly Glu
                645                 650                 655

Lys Ile Ser Tyr Gly Gly Asn Lys Lys Ala Asn Val Ser Ala Glu Leu
```

-continued

```
            660                 665                 670

Leu Phe Pro Met Pro Gly Ala Lys Asp Ala Arg Thr Val Arg Leu Ser
        675                 680                 685

Leu Phe Ala Asp Ala Gly Ser Val Trp Asp Gly Arg Thr Tyr Thr Ala
    690                 695                 700

Ala Glu Asn Gly Asn Asn Lys Ser Val Tyr Ser Glu Asn Ala His Lys
705                 710                 715                 720
Ser Thr Phe Thr Asn Glu Leu Arg Tyr Ser Ala Gly Gly Ala Val Thr
                725                 730                 735
Trp Leu Ser Pro Leu Gly Pro Met Lys Phe Ser Tyr Ala Tyr Pro Leu
            740                 745                 750
Lys Lys Lys Pro Glu Asp Glu Ile Gln Arg Phe Gln Phe Gln Leu Gly
        755                 760                 765

Thr Thr Phe
    770

<210> SEQ ID NO 10
<211> LENGTH: 2394
<212> TYPE: DNA
<213> ORGANISM: Neisseria gonorrhoeae

<400> SEQUENCE: 10
atgaaactga aacagattgc ttccgcactg atggtcttgg gcatatcgcc tttggcactt      60
gccgacttca ccatccaaga catccgcgtc gaaggcttgc agcgtaccga gccgagtacc     120
gtattcaact acctgcccgt caaagtcggc gacacctaca acgacacaca cggcagtgcc     180
atcatcaaaa gcctgtacgc caccggtttc tttgacgacg tacgcgtcga aactgcggac     240
gggcagctcc tgctgaccgt tatcgaacgc cccaccatcg gctcgctcaa catcaccggc     300
gcaaaaatgc tgcaaaacga cgccattaag aaaaacctcg aatcgttcgg gctggcgcag     360
tcgcaatact ttaatcaggc gacactcaat caggcagtcg ccggcctgaa agaagaatac     420
ctcgggcgcg gcaaactcaa tatccaaatc acgcccaaag taaccaaact cgcccgcaac     480
cgcgtcgaca tcgacatcac gattgacgag ggcaaatccg ccaaaatcac cgacatcgaa     540
tttgaaggca accaagtcta ttccgaccgc aaactgatgc ggcagatgtc gctgaccgaa     600
ggcggcattt ggacatggct gacacgaagc aaccaattca acgagcagaa atttgcccaa     660
gacatggaaa aagtaaccga cttctaccag aacaacggct acttcgattt ccgcatcctc     720
gataccgaca tccaaaccaa cgaagacaaa accaagcaga ccatcaaaat caccgtccac     780
gaaggcggac gtttccgttg gggcaaagtc tccatcgaag gcgacaccaa cgaagtcccc     840
aaagccgaac tggaaaaact gctgaccatg aagcccggca aatggtacga acgccagcag     900
atgaccgccg ttttgggtga gattcagaac cgcatgggct cggcaggcta cgcatacagc     960
gaaatcagcg tacagccgct gccaaacgcc gaaaccaaaa ccgtcgattt cgtcctgcac    1020
atcgaaccgg gccggaaaat ctacgtcaac gaaatccaca tcaccggcaa caacaaaacc    1080
cgcgacgaag tcgtgcgccg cgaattgcgc caaatggaat ccgcgcctta cgacacctcc    1140
aagctgcaac gctccaaaga gcgcgtcgag cttttgggct acttcgacaa cgtacagttt    1200
gatgccgtcc cgcttgccgg cacacccgac aaagtcgatt tgaacatgag cctgaccgaa    1260
cgttccaccg gctcgctcga cttgagcgcg ggctgggtac aggataccgg cctggtcatg    1320
tccgcaggcg tttcccaaga caacctgttc ggtacgggca agtcggccgc cctgcgcgcc    1380
tcacgaagca aaaccacgct caacggctcg ctgtcgttta ccgacccgta cttcacggca    1440
```

-continued

```
gacggggtca gcctgggcta cgatgtttac ggaaaagcct tcgacccgcg caaagcatcg    1500
accagcatca acaatataa aaccaccacg gcaggcgcag gcatccgcat gagcgtgcct    1560
gttaccgaat cgaccgcgt gaatttcggt ttggtggcag aacacctgac cgtcaacacc    1620
tacaacaaag cgcccaaaca ctatgccgac tttatcaaga aatacggcaa aaccgacggc    1680
acagacggca gcttcaaagg ctggctgtac aaaggtaccg tcggctgggg cgcaacaaa    1740 accgacagcg cgttatggcc gacgcgcggc tacctgacgg gcgtgaacgc cgaaatcgcc    1800
ctgcccggca gcaaactgca atactactcc gccacccaca accaaacctg gttcttcccc    1860
ttaagcaaaa ccttcacgct gatgctcggc ggcgaagtcg gcattgcggg cggctacggc    1920
agaaccaaag aaatccccct ctttgaaaac ttctacggcg gcggcctggg ttcggtgcgc    1980
ggatacgaaa gcggcacgct cggtccgaaa gtgtatgacg aatacggcga aaaatcagc    2040 tacggcggca caaaaaagc caacgtctcc gccgagctgc tcttcccgat gcccggcgcg    2100
aaagacgcgc gcaccgtccg cctgagcctg tttgccgacg caggcagcgt gtgggacggc    2160
aaaacctacg acgacaacag cagttccgcg accggcggca gggttcaaaa catttacggc    2220
gccggcaata cccataaatc caccttacc aacgaattgc gctattccgc cggcggcgcg    2280
gttacctggc tctcgccttt aggcccgatg aaattcagct acgcctaccc gctgaagaaa    2340
aaaccggaag acgaaatcca acgcttccaa ttccaactcg gcacgacgtt ctaa          2394
```

<210> SEQ ID NO 11
<211> LENGTH: 797
<212> TYPE: PRT
<213> ORGANISM: Neisseria gonorrhoeae

<400> SEQUENCE: 11

```
Met Lys Leu Lys Gln Ile Ala Ser Ala Leu Met Val Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205
```

-continued

```
Arg Ser Asn Gln Phe Asn Glu Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
            420                 425                 430

Val Gln Asp Thr Gly Leu Val Met Ser Ala Gly Val Ser Gln Asp Asn
    435                 440                 445

Leu Phe Gly Thr Gly Lys Ser Ala Ala Leu Arg Ala Ser Arg Ser Lys
450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Ala Gly
            500                 505                 510

Ala Gly Ile Arg Met Ser Val Pro Val Thr Glu Tyr Asp Arg Val Asn
    515                 520                 525

Phe Gly Leu Val Ala Glu His Leu Thr Val Asn Thr Tyr Asn Lys Ala
530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
    595                 600                 605

Tyr Ser Ala Thr His Asn Gln Thr Trp Phe Phe Pro Leu Ser Lys Thr
610                 615                 620

Phe Thr Leu Met Leu Gly Gly Glu Val Gly Ile Ala Gly Gly Tyr Gly
```

```
                625                 630                 635                 640
Arg Thr Lys Glu Ile Pro Phe Phe Glu Asn Phe Tyr Gly Gly Gly Leu
                    645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
                675                 680                 685

Val Ser Ala Glu Leu Leu Phe Pro Met Pro Gly Ala Lys Asp Ala Arg
        690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ser Ala Thr Gly Gly Arg Val Gln
                725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
        755                 760                 765

Pro Met Lys Phe Ser Tyr Ala Tyr Pro Leu Lys Lys Lys Pro Glu Asp
    770                 775                 780

Glu Ile Gln Arg Phe Gln Phe Gln Leu Gly Thr Thr Phe
785                 790                 795

<210> SEQ ID NO 12
<211> LENGTH: 21
<212> TYPE: PRT
<213> ORGANISM: Neisseria gonorrhoeae

<400> SEQUENCE: 12

Met Lys Leu Lys Gln Ile Ala Ser Ala Leu Met Val Leu Gly Ile Ser
1               5                   10                  15

Pro Leu Ala Leu Ala
            20

<210> SEQ ID NO 13
<211> LENGTH: 776
<212> TYPE: PRT
<213> ORGANISM: Neisseria gonorrhoeae

<400> SEQUENCE: 13

Asp Phe Thr Ile Gln Asp Ile Arg Val Glu Gly Leu Gln Arg Thr Glu
1               5                   10                  15

Pro Ser Thr Val Phe Asn Tyr Leu Pro Val Lys Val Gly Asp Thr Tyr
            20                  25                  30

Asn Asp Thr His Gly Ser Ala Ile Ile Lys Ser Leu Tyr Ala Thr Gly
        35                  40                  45

Phe Phe Asp Asp Val Arg Val Glu Thr Ala Asp Gly Gln Leu Leu Leu
    50                  55                  60

Thr Val Ile Glu Arg Pro Thr Ile Gly Ser Leu Asn Ile Thr Gly Ala
65                  70                  75                  80

Lys Met Leu Gln Asn Asp Ala Ile Lys Lys Asn Leu Glu Ser Phe Gly
                85                  90                  95

Leu Ala Gln Ser Gln Tyr Phe Asn Gln Ala Thr Leu Asn Gln Ala Val
            100                 105                 110

Ala Gly Leu Lys Glu Glu Tyr Leu Gly Arg Gly Lys Leu Asn Ile Gln
        115                 120                 125

Ile Thr Pro Lys Val Thr Lys Leu Ala Arg Asn Arg Val Asp Ile Asp
```

-continued

```
            130                 135                 140
Ile Thr Ile Asp Glu Gly Lys Ser Ala Lys Ile Thr Asp Ile Glu Phe
145                 150                 155                 160

Glu Gly Asn Gln Val Tyr Ser Asp Arg Lys Leu Met Arg Gln Met Ser
                165                 170                 175

Leu Thr Glu Gly Gly Ile Trp Thr Trp Leu Thr Arg Ser Asn Gln Phe
            180                 185                 190

Asn Glu Gln Lys Phe Ala Gln Asp Met Glu Lys Val Thr Asp Phe Tyr
        195                 200                 205

Gln Asn Asn Gly Tyr Phe Asp Phe Arg Ile Leu Asp Thr Asp Ile Gln
    210                 215                 220

Thr Asn Glu Asp Lys Thr Lys Gln Thr Ile Lys Ile Thr Val His Glu
225                 230                 235                 240

Gly Gly Arg Phe Arg Trp Gly Lys Val Ser Ile Glu Gly Asp Thr Asn
                245                 250                 255

Glu Val Pro Lys Ala Glu Leu Glu Lys Leu Leu Thr Met Lys Pro Gly
            260                 265                 270

Lys Trp Tyr Glu Arg Gln Gln Met Thr Ala Val Leu Gly Glu Ile Gln
        275                 280                 285

Asn Arg Met Gly Ser Ala Gly Tyr Ala Tyr Ser Glu Ile Ser Val Gln
    290                 295                 300

Pro Leu Pro Asn Ala Glu Thr Lys Thr Val Asp Phe Val Leu His Ile
305                 310                 315                 320

Glu Pro Gly Arg Lys Ile Tyr Val Asn Glu Ile His Ile Thr Gly Asn
                325                 330                 335

Asn Lys Thr Arg Asp Glu Val Val Arg Arg Glu Leu Arg Gln Met Glu
            340                 345                 350

Ser Ala Pro Tyr Asp Thr Ser Lys Leu Gln Arg Ser Lys Glu Arg Val
        355                 360                 365

Glu Leu Leu Gly Tyr Phe Asp Asn Val Gln Phe Asp Ala Val Pro Leu
    370                 375                 380

Ala Gly Thr Pro Asp Lys Val Asp Leu Asn Met Ser Leu Thr Glu Arg
385                 390                 395                 400

Ser Thr Gly Ser Leu Asp Leu Ser Ala Gly Trp Val Gln Asp Thr Gly
                405                 410                 415

Leu Val Met Ser Ala Gly Val Ser Gln Asp Asn Leu Phe Gly Thr Gly
            420                 425                 430

Lys Ser Ala Ala Leu Arg Ala Ser Arg Ser Lys Thr Thr Leu Asn Gly
        435                 440                 445

Ser Leu Ser Phe Thr Asp Pro Tyr Phe Thr Ala Asp Gly Val Ser Leu
    450                 455                 460

Gly Tyr Asp Val Tyr Gly Lys Ala Phe Asp Pro Arg Lys Ala Ser Thr
465                 470                 475                 480

Ser Ile Lys Gln Tyr Lys Thr Thr Thr Ala Gly Ala Gly Ile Arg Met
                485                 490                 495

Ser Val Pro Val Thr Glu Tyr Asp Arg Val Asn Phe Gly Leu Val Ala
            500                 505                 510

Glu His Leu Thr Val Asn Thr Tyr Asn Lys Ala Pro Lys His Tyr Ala
        515                 520                 525

Asp Phe Ile Lys Lys Tyr Gly Lys Thr Asp Gly Thr Asp Gly Ser Phe
    530                 535                 540

Lys Gly Trp Leu Tyr Lys Gly Thr Val Gly Trp Gly Arg Asn Lys Thr
545                 550                 555                 560
```

-continued

```
Asp Ser Ala Leu Trp Pro Thr Arg Gly Tyr Leu Thr Gly Val Asn Ala
            565                 570                 575

Glu Ile Ala Leu Pro Gly Ser Lys Leu Gln Tyr Tyr Ser Ala Thr His
            580                 585                 590

Asn Gln Thr Trp Phe Phe Pro Leu Ser Lys Thr Phe Thr Leu Met Leu
            595                 600                 605

Gly Gly Glu Val Gly Ile Ala Gly Gly Tyr Gly Arg Thr Lys Glu Ile
            610                 615                 620

Pro Phe Phe Glu Asn Phe Tyr Gly Gly Leu Gly Ser Val Arg Gly
625                 630                 635                 640

Tyr Glu Ser Gly Thr Leu Gly Pro Lys Val Tyr Asp Glu Tyr Gly Glu
            645                 650                 655

Lys Ile Ser Tyr Gly Gly Asn Lys Lys Ala Asn Val Ser Ala Glu Leu
            660                 665                 670

Leu Phe Pro Met Pro Gly Ala Lys Asp Ala Arg Thr Val Arg Leu Ser
            675                 680                 685

Leu Phe Ala Asp Ala Gly Ser Val Trp Asp Gly Lys Thr Tyr Asp Asp
            690                 695                 700

Asn Ser Ser Ser Ala Thr Gly Gly Arg Val Gln Asn Ile Tyr Gly Ala
705                 710                 715                 720

Gly Asn Thr His Lys Ser Thr Phe Thr Asn Glu Leu Arg Tyr Ser Ala
            725                 730                 735

Gly Gly Ala Val Thr Trp Leu Ser Pro Leu Gly Pro Met Lys Phe Ser
            740                 745                 750

Tyr Ala Tyr Pro Leu Lys Lys Lys Pro Glu Asp Glu Ile Gln Arg Phe
            755                 760                 765

Gln Phe Gln Leu Gly Thr Thr Phe
            770                 775

<210> SEQ ID NO 14
<211> LENGTH: 5
<212> TYPE: PRT
<213> ORGANISM: Neisseria meningitidis

<400> SEQUENCE: 14

Gly Leu Gln Arg Thr
1               5

<210> SEQ ID NO 15
<211> LENGTH: 9
<212> TYPE: PRT
<213> ORGANISM: Neisseria meningitidis

<400> SEQUENCE: 15

Lys Val Gly Asp Thr Tyr Asn Asp Thr
1               5

<210> SEQ ID NO 16
<211> LENGTH: 6
<212> TYPE: PRT
<213> ORGANISM: Neisseria meningitidis

<400> SEQUENCE: 16

Phe Phe Asp Asp Val Arg
1               5

<210> SEQ ID NO 17
<211> LENGTH: 5
```

```
<212> TYPE: PRT
<213> ORGANISM: Neisseria meningitidis

<400> SEQUENCE: 17

Gln Ala Val Ala Gly
1               5

<210> SEQ ID NO 18
<211> LENGTH: 12
<212> TYPE: PRT
<213> ORGANISM: Neisseria meningitidis

<400> SEQUENCE: 18

Ala Gly Leu Asp Met Glu Lys Val Thr Asp Phe Tyr
1               5                   10

<210> SEQ ID NO 19
<211> LENGTH: 10
<212> TYPE: PRT
<213> ORGANISM: Neisseria meningitidis

<400> SEQUENCE: 19

Lys Ala Glu Leu Glu Lys Leu Leu Thr Met
1               5                   10

<210> SEQ ID NO 20
<211> LENGTH: 5
<212> TYPE: PRT
<213> ORGANISM: Neisseria meningitidis

<400> SEQUENCE: 20

Pro Gly Lys Trp Tyr
1               5

<210> SEQ ID NO 21
<211> LENGTH: 9
<212> TYPE: PRT
<213> ORGANISM: Neisseria meningitidis

<400> SEQUENCE: 21

Ala Val Leu Gly Glu Ile Gln Asn Arg
1               5

<210> SEQ ID NO 22
<211> LENGTH: 6
<212> TYPE: PRT
<213> ORGANISM: Neisseria meningitidis

<400> SEQUENCE: 22

Arg Glu Leu Arg Gln Met
1               5

<210> SEQ ID NO 23
<211> LENGTH: 7
<212> TYPE: PRT
<213> ORGANISM: Neisseria meningitidis

<400> SEQUENCE: 23

Thr Ser Lys Leu Gln Arg Ser
1               5

<210> SEQ ID NO 24
<211> LENGTH: 8
<212> TYPE: PRT
<213> ORGANISM: Neisseria meningitidis
```

-continued

```
<400> SEQUENCE: 24

Leu Gly Tyr Phe Asp Asn Val Gln
1               5

<210> SEQ ID NO 25
<211> LENGTH: 23
<212> TYPE: PRT
<213> ORGANISM: Neisseria meningitidis

<400> SEQUENCE: 25

Thr Val Asn Thr Tyr Asn Lys Ala Pro Lys His Tyr Ala Asp Phe Ile
1               5                   10                  15

Lys Lys Tyr Gly Lys Thr Asp
            20

<210> SEQ ID NO 26
<211> LENGTH: 6
<212> TYPE: PRT
<213> ORGANISM: Neisseria meningitidis

<400> SEQUENCE: 26

Gly Ser Phe Lys Gly Trp
1               5

<210> SEQ ID NO 27
<211> LENGTH: 8
<212> TYPE: PRT
<213> ORGANISM: Neisseria meningitidis

<400> SEQUENCE: 27

Gly Ser Val Arg Gly Tyr Glu Ser
1               5

<210> SEQ ID NO 28
<211> LENGTH: 10
<212> TYPE: PRT
<213> ORGANISM: Neisseria meningitidis

<400> SEQUENCE: 28

Pro Lys Val Tyr Asp Glu Tyr Gly Glu Lys
1               5                   10

<210> SEQ ID NO 29
<211> LENGTH: 10
<212> TYPE: PRT
<213> ORGANISM: Neisseria meningitidis

<400> SEQUENCE: 29

Gly Arg Val Gln Asn Ile Tyr Gly Ala Gly
1               5                   10

<210> SEQ ID NO 30
<211> LENGTH: 5
<212> TYPE: PRT
<213> ORGANISM: Neisseria meningitidis

<400> SEQUENCE: 30

His Lys Ser Thr Phe
1               5

<210> SEQ ID NO 31
<211> LENGTH: 8
<212> TYPE: PRT
```

<213> ORGANISM: Neisseria meningitidis

<400> SEQUENCE: 31

Thr Trp Leu Ser Pro Leu Gly Pro
1               5

<210> SEQ ID NO 32
<211> LENGTH: 5
<212> TYPE: PRT
<213> ORGANISM: Neisseria meningitidis

<400> SEQUENCE: 32

Lys Pro Glu Asp Glu
1               5

<210> SEQ ID NO 33
<211> LENGTH: 5
<212> TYPE: PRT
<213> ORGANISM: Neisseria meningitidis

<400> SEQUENCE: 33

Met Lys Leu Lys Gln
1               5

<210> SEQ ID NO 34
<211> LENGTH: 14
<212> TYPE: PRT
<213> ORGANISM: Neisseria meningitidis

<400> SEQUENCE: 34

Asp Ile Arg Val Glu Gly Leu Gln Arg Thr Glu Pro Ser Thr
1               5                   10

<210> SEQ ID NO 35
<211> LENGTH: 11
<212> TYPE: PRT
<213> ORGANISM: Neisseria meningitidis

<400> SEQUENCE: 35

Lys Val Gly Asp Thr Tyr Asn Asp Thr His Gly
1               5                   10

<210> SEQ ID NO 36
<211> LENGTH: 10
<212> TYPE: PRT
<213> ORGANISM: Neisseria meningitidis

<400> SEQUENCE: 36

Asp Asp Val Arg Val Glu Thr Ala Asp Gly
1               5                   10

<210> SEQ ID NO 37
<211> LENGTH: 6
<212> TYPE: PRT
<213> ORGANISM: Neisseria meningitidis

<400> SEQUENCE: 37

Ile Glu Arg Pro Thr Ile
1               5

<210> SEQ ID NO 38
<211> LENGTH: 14
<212> TYPE: PRT
<213> ORGANISM: Neisseria meningitidis

```
<400> SEQUENCE: 38

Lys Met Leu Gln Asn Asp Ala Ile Lys Lys Asn Leu Glu Ser
1               5                   10

<210> SEQ ID NO 39
<211> LENGTH: 13
<212> TYPE: PRT
<213> ORGANISM: Neisseria meningitidis

<400> SEQUENCE: 39

Gly Leu Lys Glu Glu Tyr Leu Gly Arg Gly Lys Leu Asn
1               5                   10

<210> SEQ ID NO 40
<211> LENGTH: 12
<212> TYPE: PRT
<213> ORGANISM: Neisseria meningitidis

<400> SEQUENCE: 40

Lys Val Thr Lys Leu Ala Arg Asn Arg Val Asp Ile
1               5                   10

<210> SEQ ID NO 41
<211> LENGTH: 29
<212> TYPE: PRT
<213> ORGANISM: Neisseria meningitidis

<400> SEQUENCE: 41

Ile Thr Ile Asp Glu Gly Lys Ser Ala Lys Ile Thr Asp Ile Glu Phe
1               5                   10                  15

Glu Gly Asn Gln Val Tyr Ser Asp Arg Lys Leu Met Arg
            20                  25

<210> SEQ ID NO 42
<211> LENGTH: 19
<212> TYPE: PRT
<213> ORGANISM: Neisseria meningitidis

<400> SEQUENCE: 42

Thr Arg Ser Asn Gln Phe Asn Glu Gln Lys Phe Ala Gln Asp Met Glu
1               5                   10                  15

Lys Val Thr

<210> SEQ ID NO 43
<211> LENGTH: 6
<212> TYPE: PRT
<213> ORGANISM: Neisseria meningitidis

<400> SEQUENCE: 43

Tyr Gln Asn Asn Gly Tyr
1               5

<210> SEQ ID NO 44
<211> LENGTH: 18
<212> TYPE: PRT
<213> ORGANISM: Neisseria meningitidis

<400> SEQUENCE: 44

Arg Ile Leu Asp Thr Asp Ile Gln Thr Asn Glu Asp Lys Thr Lys Gln
1               5                   10                  15

Thr Ile
```

```
<210> SEQ ID NO 45
<211> LENGTH: 9
<212> TYPE: PRT
<213> ORGANISM: Neisseria meningitidis

<400> SEQUENCE: 45

Val His Glu Gly Gly Arg Phe Arg Trp
1               5

<210> SEQ ID NO 46
<211> LENGTH: 16
<212> TYPE: PRT
<213> ORGANISM: Neisseria meningitidis

<400> SEQUENCE: 46

Ser Ile Glu Gly Asp Thr Asn Glu Val Pro Lys Ala Glu Leu Glu Lys
1               5                   10                  15

<210> SEQ ID NO 47
<211> LENGTH: 10
<212> TYPE: PRT
<213> ORGANISM: Neisseria meningitidis

<400> SEQUENCE: 47

Lys Pro Gly Lys Trp Tyr Glu Arg Gln Gln
1               5                   10

<210> SEQ ID NO 48
<211> LENGTH: 9
<212> TYPE: PRT
<213> ORGANISM: Neisseria meningitidis

<400> SEQUENCE: 48

Ile Gln Asn Arg Met Gly Ser Ala Gly
1               5

<210> SEQ ID NO 49
<211> LENGTH: 9
<212> TYPE: PRT
<213> ORGANISM: Neisseria meningitidis

<400> SEQUENCE: 49

Pro Leu Pro Asn Ala Glu Thr Lys Thr
1               5

<210> SEQ ID NO 50
<211> LENGTH: 8
<212> TYPE: PRT
<213> ORGANISM: Neisseria meningitidis

<400> SEQUENCE: 50

Ile Glu Pro Gly Arg Lys Ile Tyr
1               5

<210> SEQ ID NO 51
<211> LENGTH: 37
<212> TYPE: PRT
<213> ORGANISM: Neisseria meningitidis

<400> SEQUENCE: 51

Ile Thr Gly Asn Asn Lys Thr Arg Asp Glu Val Val Arg Arg Glu Leu
1               5                   10                  15

Arg Gln Met Glu Ser Ala Pro Tyr Asp Thr Ser Lys Leu Gln Arg Ser
            20                  25                  30
```

```
Lys Glu Arg Val Glu
        35

<210> SEQ ID NO 52
<211> LENGTH: 9
<212> TYPE: PRT
<213> ORGANISM: Neisseria meningitidis

<400> SEQUENCE: 52

Ala Gly Thr Pro Asp Lys Val Asp Leu
1               5

<210> SEQ ID NO 53
<211> LENGTH: 11
<212> TYPE: PRT
<213> ORGANISM: Neisseria meningitidis

<400> SEQUENCE: 53

Met Ser Leu Thr Glu Arg Ser Thr Gly Ser Leu
1               5                  10

<210> SEQ ID NO 54
<211> LENGTH: 25
<212> TYPE: PRT
<213> ORGANISM: Neisseria meningitidis

<400> SEQUENCE: 54

Gly Val Ser Gln Asp Asn Leu Phe Gly Thr Gly Lys Ser Ala Ala Leu
1               5                   10                  15

Arg Ala Ser Arg Ser Lys Thr Thr Leu
            20                  25

<210> SEQ ID NO 55
<211> LENGTH: 22
<212> TYPE: PRT
<213> ORGANISM: Neisseria meningitidis

<400> SEQUENCE: 55

Val Tyr Gly Lys Ala Phe Asp Pro Arg Lys Ala Ser Thr Ser Ile Lys
1               5                   10                  15

Gln Tyr Lys Thr Thr Thr
            20

<210> SEQ ID NO 56
<211> LENGTH: 8
<212> TYPE: PRT
<213> ORGANISM: Neisseria meningitidis

<400> SEQUENCE: 56

Thr Glu Tyr Asp Arg Val Asn Phe
1               5

<210> SEQ ID NO 57
<211> LENGTH: 10
<212> TYPE: PRT
<213> ORGANISM: Neisseria meningitidis

<400> SEQUENCE: 57

Asn Thr Tyr Asn Lys Ala Pro Lys His Tyr
1               5                   10

<210> SEQ ID NO 58
<211> LENGTH: 15
<212> TYPE: PRT
```

-continued

<213> ORGANISM: Neisseria meningitidis

<400> SEQUENCE: 58

```
Phe Ile Lys Lys Tyr Gly Lys Thr Asp Gly Thr Asp Gly Ser Phe
1               5                   10                  15
```

<210> SEQ ID NO 59
<211> LENGTH: 10
<212> TYPE: PRT
<213> ORGANISM: Neisseria meningitidis

<400> SEQUENCE: 59

```
Val Gly Trp Gly Arg Asn Lys Thr Asp Ser
1               5                   10
```

<210> SEQ ID NO 60
<211> LENGTH: 5
<212> TYPE: PRT
<213> ORGANISM: Neisseria meningitidis

<400> SEQUENCE: 60

```
Leu Pro Gly Ser Lys
1               5
```

<210> SEQ ID NO 61
<211> LENGTH: 5
<212> TYPE: PRT
<213> ORGANISM: Neisseria meningitidis

<400> SEQUENCE: 61

```
Thr His Asn Gln Thr
1               5
```

<210> SEQ ID NO 62
<211> LENGTH: 10
<212> TYPE: PRT
<213> ORGANISM: Neisseria meningitidis

<400> SEQUENCE: 62

```
Gly Gly Tyr Gly Arg Thr Lys Glu Ile Pro
1               5                   10
```

<210> SEQ ID NO 63
<211> LENGTH: 5
<212> TYPE: PRT
<213> ORGANISM: Neisseria meningitidis

<400> SEQUENCE: 63

```
Phe Tyr Gly Gly Gly
1               5
```

<210> SEQ ID NO 64
<211> LENGTH: 33
<212> TYPE: PRT
<213> ORGANISM: Neisseria meningitidis

<400> SEQUENCE: 64

```
Gly Ser Val Arg Gly Tyr Glu Ser Gly Thr Leu Gly Pro Lys Val Tyr
1               5                   10                  15

Asp Glu Tyr Gly Glu Lys Ile Ser Tyr Gly Gly Asn Lys Lys Ala Asn
            20                  25                  30

Val
```

```
<210> SEQ ID NO 65
<211> LENGTH: 10
<212> TYPE: PRT
<213> ORGANISM: Neisseria meningitidis

<400> SEQUENCE: 65

Pro Gly Ala Lys Asp Ala Arg Thr Val Arg
1               5                   10

<210> SEQ ID NO 66
<211> LENGTH: 25
<212> TYPE: PRT
<213> ORGANISM: Neisseria meningitidis

<400> SEQUENCE: 66

Asp Ala Gly Ser Val Trp Asp Gly Lys Thr Tyr Asp Asp Asn Ser Ser
1               5                   10                  15

Ser Ala Thr Gly Gly Arg Val Gln Asn
            20                  25

<210> SEQ ID NO 67
<211> LENGTH: 10
<212> TYPE: PRT
<213> ORGANISM: Neisseria meningitidis

<400> SEQUENCE: 67

Gly Ala Gly Asn Thr His Lys Ser Thr Phe
1               5                   10

<210> SEQ ID NO 68
<211> LENGTH: 9
<212> TYPE: PRT
<213> ORGANISM: Neisseria meningitidis

<400> SEQUENCE: 68

Asn Glu Leu Arg Tyr Ser Ala Gly Gly
1               5

<210> SEQ ID NO 69
<211> LENGTH: 6
<212> TYPE: PRT
<213> ORGANISM: Neisseria meningitidis

<400> SEQUENCE: 69

Ser Pro Leu Gly Pro Met
1               5

<210> SEQ ID NO 70
<211> LENGTH: 12
<212> TYPE: PRT
<213> ORGANISM: Neisseria meningitidis

<400> SEQUENCE: 70

Tyr Pro Leu Lys Lys Lys Pro Glu Asp Glu Ile Gln
1               5                   10

<210> SEQ ID NO 71
<211> LENGTH: 5
<212> TYPE: PRT
<213> ORGANISM: Neisseria meningitidis

<400> SEQUENCE: 71

Met Lys Leu Lys Gln
1               5
```

<210> SEQ ID NO 72
<211> LENGTH: 12
<212> TYPE: PRT
<213> ORGANISM: Neisseria meningitidis

<400> SEQUENCE: 72

Asp Ile Arg Val Glu Gly Leu Gln Arg Thr Glu Pro
1               5                   10

<210> SEQ ID NO 73
<211> LENGTH: 7
<212> TYPE: PRT
<213> ORGANISM: Neisseria meningitidis

<400> SEQUENCE: 73

Lys Val Gly Asp Thr Tyr Asn
1               5

<210> SEQ ID NO 74
<211> LENGTH: 9
<212> TYPE: PRT
<213> ORGANISM: Neisseria meningitidis

<400> SEQUENCE: 74

Asp Asp Val Arg Val Glu Thr Ala Asp
1               5

<210> SEQ ID NO 75
<211> LENGTH: 5
<212> TYPE: PRT
<213> ORGANISM: Neisseria meningitidis

<400> SEQUENCE: 75

Ile Glu Arg Pro Thr
1               5

<210> SEQ ID NO 76
<211> LENGTH: 8
<212> TYPE: PRT
<213> ORGANISM: Neisseria meningitidis

<400> SEQUENCE: 76

Asp Ala Ile Lys Lys Asn Leu Glu
1               5

<210> SEQ ID NO 77
<211> LENGTH: 12
<212> TYPE: PRT
<213> ORGANISM: Neisseria meningitidis

<400> SEQUENCE: 77

Gly Leu Lys Glu Glu Tyr Leu Gly Arg Gly Lys Leu
1               5                   10

<210> SEQ ID NO 78
<211> LENGTH: 12
<212> TYPE: PRT
<213> ORGANISM: Neisseria meningitidis

<400> SEQUENCE: 78

Lys Val Thr Lys Leu Ala Arg Asn Arg Val Asp Ile
1               5                   10

<210> SEQ ID NO 79

```
<211> LENGTH: 18
<212> TYPE: PRT
<213> ORGANISM: Neisseria meningitidis

<400> SEQUENCE: 79

Ile Thr Ile Asp Glu Gly Lys Ser Ala Lys Ile Thr Asp Ile Glu Phe
1               5                   10                  15

Glu Gly

<210> SEQ ID NO 80
<211> LENGTH: 8
<212> TYPE: PRT
<213> ORGANISM: Neisseria meningitidis

<400> SEQUENCE: 80

Tyr Ser Asp Arg Lys Leu Met Arg
1               5

<210> SEQ ID NO 81
<211> LENGTH: 16
<212> TYPE: PRT
<213> ORGANISM: Neisseria meningitidis

<400> SEQUENCE: 81

Asn Gln Phe Asn Glu Gln Lys Phe Ala Gln Asp Met Glu Lys Val Thr
1               5                   10                  15

<210> SEQ ID NO 82
<211> LENGTH: 18
<212> TYPE: PRT
<213> ORGANISM: Neisseria meningitidis

<400> SEQUENCE: 82

Arg Ile Leu Asp Thr Asp Ile Gln Thr Asn Glu Asp Lys Thr Lys Gln
1               5                   10                  15

Thr Ile

<210> SEQ ID NO 83
<211> LENGTH: 7
<212> TYPE: PRT
<213> ORGANISM: Neisseria meningitidis

<400> SEQUENCE: 83

Glu Gly Gly Arg Phe Arg Trp
1               5

<210> SEQ ID NO 84
<211> LENGTH: 16
<212> TYPE: PRT
<213> ORGANISM: Neisseria meningitidis

<400> SEQUENCE: 84

Ser Ile Glu Gly Asp Thr Asn Glu Val Pro Lys Ala Glu Leu Glu Lys
1               5                   10                  15

<210> SEQ ID NO 85
<211> LENGTH: 6
<212> TYPE: PRT
<213> ORGANISM: Neisseria meningitidis

<400> SEQUENCE: 85

Ile Gln Asn Arg Met Gly
1               5
```

```
<210> SEQ ID NO 86
<211> LENGTH: 7
<212> TYPE: PRT
<213> ORGANISM: Neisseria meningitidis

<400> SEQUENCE: 86

Pro Asn Ala Glu Thr Lys Thr
1               5

<210> SEQ ID NO 87
<211> LENGTH: 7
<212> TYPE: PRT
<213> ORGANISM: Neisseria meningitidis

<400> SEQUENCE: 87

Glu Pro Gly Arg Lys Ile Tyr
1               5

<210> SEQ ID NO 88
<211> LENGTH: 18
<212> TYPE: PRT
<213> ORGANISM: Neisseria meningitidis

<400> SEQUENCE: 88

Gly Asn Asn Lys Thr Arg Asp Glu Val Val Arg Arg Glu Leu Arg Gln
1               5                   10                  15

Met Glu

<210> SEQ ID NO 89
<211> LENGTH: 16
<212> TYPE: PRT
<213> ORGANISM: Neisseria meningitidis

<400> SEQUENCE: 89

Ala Pro Tyr Asp Thr Ser Lys Leu Gln Arg Ser Lys Glu Arg Val Glu
1               5                   10                  15

<210> SEQ ID NO 90
<211> LENGTH: 8
<212> TYPE: PRT
<213> ORGANISM: Neisseria meningitidis

<400> SEQUENCE: 90

Gly Thr Pro Asp Lys Val Asp Leu
1               5

<210> SEQ ID NO 91
<211> LENGTH: 7
<212> TYPE: PRT
<213> ORGANISM: Neisseria meningitidis

<400> SEQUENCE: 91

Leu Thr Glu Arg Ser Thr Gly
1               5

<210> SEQ ID NO 92
<211> LENGTH: 14
<212> TYPE: PRT
<213> ORGANISM: Neisseria meningitidis

<400> SEQUENCE: 92

Lys Ser Ala Ala Leu Arg Ala Ser Arg Ser Lys Thr Thr Leu
1               5                   10
```

```
<210> SEQ ID NO 93
<211> LENGTH: 10
<212> TYPE: PRT
<213> ORGANISM: Neisseria meningitidis

<400> SEQUENCE: 93

Ala Phe Asp Pro Arg Lys Ala Ser Thr Ser
1               5                   10

<210> SEQ ID NO 94
<211> LENGTH: 5
<212> TYPE: PRT
<213> ORGANISM: Neisseria meningitidis

<400> SEQUENCE: 94

Thr Glu Tyr Asp Arg
1               5

<210> SEQ ID NO 95
<211> LENGTH: 7
<212> TYPE: PRT
<213> ORGANISM: Neisseria meningitidis

<400> SEQUENCE: 95

Asn Lys Ala Pro Lys His Tyr
1               5

<210> SEQ ID NO 96
<211> LENGTH: 15
<212> TYPE: PRT
<213> ORGANISM: Neisseria meningitidis

<400> SEQUENCE: 96

Phe Ile Lys Lys Tyr Gly Lys Thr Asp Gly Thr Asp Gly Ser Phe
1               5                   10                  15

<210> SEQ ID NO 97
<211> LENGTH: 7
<212> TYPE: PRT
<213> ORGANISM: Neisseria meningitidis

<400> SEQUENCE: 97

Gly Arg Asn Lys Thr Asp Ser
1               5

<210> SEQ ID NO 98
<211> LENGTH: 5
<212> TYPE: PRT
<213> ORGANISM: Neisseria meningitidis

<400> SEQUENCE: 98

Gly Arg Thr Lys Glu
1               5

<210> SEQ ID NO 99
<211> LENGTH: 8
<212> TYPE: PRT
<213> ORGANISM: Neisseria meningitidis

<400> SEQUENCE: 99

Lys Val Tyr Asp Glu Tyr Gly Glu
1               5

<210> SEQ ID NO 100
```

```
<211> LENGTH: 7
<212> TYPE: PRT
<213> ORGANISM: Neisseria meningitidis

<400> SEQUENCE: 100

Gly Asn Lys Lys Ala Asn Val
1               5

<210> SEQ ID NO 101
<211> LENGTH: 9
<212> TYPE: PRT
<213> ORGANISM: Neisseria meningitidis

<400> SEQUENCE: 101

Gly Ala Lys Asp Ala Arg Thr Val Arg
1               5

<210> SEQ ID NO 102
<211> LENGTH: 9
<212> TYPE: PRT
<213> ORGANISM: Neisseria meningitidis

<400> SEQUENCE: 102

Lys Thr Tyr Asp Asp Asn Ser Ser Ser
1               5

<210> SEQ ID NO 103
<211> LENGTH: 5
<212> TYPE: PRT
<213> ORGANISM: Neisseria meningitidis

<400> SEQUENCE: 103

Thr Gly Gly Arg Val
1               5

<210> SEQ ID NO 104
<211> LENGTH: 10
<212> TYPE: PRT
<213> ORGANISM: Neisseria meningitidis

<400> SEQUENCE: 104

Leu Lys Lys Lys Pro Glu Asp Glu Ile Gln
1               5                   10

<210> SEQ ID NO 105
<211> LENGTH: 33
<212> TYPE: DNA
<213> ORGANISM: Artificial Sequence
<220> FEATURE:
<223> OTHER INFORMATION: 'orf21 for' primer

<400> SEQUENCE: 105
cgcggatccc atatggactt caccatccaa gac                                    33

<210> SEQ ID NO 106
<211> LENGTH: 28
<212> TYPE: DNA
<213> ORGANISM: Artificial Sequence
<220> FEATURE:
<223> OTHER INFORMATION: 'orf21 rev' primer

<400> SEQUENCE: 106
cccgctcgag ttagaacgtc gtgccgag                                          28
```